(12) United States Patent
Fernandez-Chimeno et al.

(10) Patent No.: US 6,395,711 B1
(45) Date of Patent: May 28, 2002

(54) MACROLIDES WITH ANTITUMOR ACTIVITY

(75) Inventors: Rosa Isabel Fernandez-Chimeno; Francisco Romero; Jose Luis Fernandez-Puentes; Julia Perez-Baz; Librada Maria Canedo; Fernando Espliego, all of Onzonilla (ES)

(73) Assignee: Instituto Biomar S.A., Onzonilla (ES)

( * ) Notice: Subject to any disclaimer, the term of this patent is extended or adjusted under 35 U.S.C. 154(b) by 0 days.

(21) Appl. No.: 09/485,219

(22) PCT Filed: Aug. 4, 1998

(86) PCT No.: PCT/GB98/02336
§ 371 (c)(1),
(2), (4) Date: Apr. 17, 2000

(87) PCT Pub. No.: WO99/07710
PCT Pub. Date: Feb. 18, 1999

(30) Foreign Application Priority Data

Aug. 4, 1997 (GB) ............................................. 9716486

(51) Int. Cl.[7] ................... A61K 31/70; C07H 17/08; C12P 19/62; C12N 1/00

(52) U.S. Cl. ................... 514/31; 435/76; 435/867; 514/33; 514/468; 536/65; 549/298

(58) Field of Search .................. 536/65; 549/298; 514/31, 468, 33; 435/76, 867

(56) References Cited

U.S. PATENT DOCUMENTS

| 4,639,467 A | 1/1987 | Celino ........................ 514/468 |
| 5,003,056 A | 3/1991 | Nishikiori et al. ............ 536/71 |

FOREIGN PATENT DOCUMENTS

| EP | 0164207 B1 | 12/1985 |
| EP | 0322748 B1 | 4/1994 |

OTHER PUBLICATIONS

Laatsch et al., "Oligomycin F, A New Immunosuppressive Homologue of Oligomycin A", *The Journal of Antibiotics*, vol. 46, No. 9, pp. 1334–1341 (1993).
Yamazaki et al., "44–Homooligomycins A and B, New Antitumor Antibiotics From Sreptomyces bottropensis", *The Journal of Antibiotics*, vol. 45, No. 2, pp. 171–179 (1992).

*Primary Examiner*—Elli Peselev
(74) *Attorney, Agent, or Firm*—Ernst V. Linek; Banner & Witcoff, Ltd.

(57) ABSTRACT

The compound referred to herein as IB-962 12, having structure (I) can be obtained by cultivating the strain of Micromonospora sp. ES25-008, available under the accession number CECT-3333, and can be hydrolyzed to give IB-96212B having structure (II). The sugar substituent which is L-rhodinose, can its elf be derivatized or the sugar can be replaced, in either case, giving further derivatives of IB-96212 having a group other than L-rhodinose at the position of the sugar.

13 Claims, 20 Drawing Sheets

| FIG. 1A |
|---|
| FIG. 1B |
| FIG. 1C |

FIG. 1

```
WATERS 991  INTEGRATOR

C22101.DT3         06-16-1997         04:12:58         SAMPLE NAME                        WATERS
Y-SCALE                               .21 AU/FS        PAPER SPEED         C22(1-10-1)
SAMPLING TIME                         93 MSEC =16                          5 MM/MIN
SENSE                                 NORMAL           COLUMN
RESOLUTION                            3 NM             PACKING MATERIAL
TIME RANGE                            0 --- 7 MIN      MOBILE PHASE        MM ID=        MM
INTERVAL                              1.58 SEC         FLOW RATE
BASELINE                              0 --- 7 MIN      PRESSURE                          ML/MIN
SMOOTHING                             7 POINTS         SLOPE               .005  AU/MIN
DRIFT                                 .002 AU/MIN      HEIGHT              .001  AU
WIDTH                                 .02 MIN          MIN. AREA           .0001 AU*MIN
TIME DOUBLE                           30 MIN           MINUS PEAK                        OFF
```

FIG. 1A

| WATERS 991 INTEGRATOR | | | | C22101.DT3 | | WATERS |
|---|---|---|---|---|---|---|
| 06-16-1997 | | 04:12:58 | | SAMPLE NAME | | C22(1-10-1) |
| SAMPLING TIME | | 93 MSEC =16 | | BASELINE | | 0 --- 7 MIN |
| SENSE | | NORMAL | | RESOLUTION | | 3 NM |
| TIME RANGE | | 0 --- 7 MIN | | INTERVAL | | 1.58 SEC |
| SMOOTHING | | 7 POINTS | | SLOPE | | .005 AU/MIN |
| DRIFT | | .002 AU/MIN | | HEIGHT | | .001 AU |
| WIDTH | | .02 MIN | | MIN. AREA | | .0001AU*MIN |
| TIME DOUBLE | | 30 MIN | | MINUS PEAK | | OFF |
| COLUMN | MM ID | = MM | | PACKING MATERIAL | | |
| MOBILE PHASE | | | | FLOW RATE | | ML/MIN |
| PRESSURE | | | | | | |

REPORT  DATA C22101.DT3

225 NM

| NO. | RETENTION TIME | HEIGHT [AU] | LEFT TIME | RIGHT TIME | AREA [AU=MIN] | AREA [%] | MARK |
|---|---|---|---|---|---|---|---|
| 1 | 1.82 | 0.0038 | 1.66 | 2.53 | 0.000690 | 1.185 | 1 |
| 2 | 3.64 | 0.1727 | 2.90 | 5.46 | 0.057548 | 98.815 | 1 |

HPCL CHROMATOGRAM OF IB-96212

FIG. 1C $^{13}$C NMR SPECTRUM OF IB-96212

FIG. 12

MACROLIDES WITH ANTITUMOR ACTIVITY

FIELD OF THE INVENTION

The present invention relates to a novel macrolide compound isolated from the culture broth of a new marine microbial organism. The present invention further relates to the production of the novel compound by aerobic fermentation under controlled conditions and its isolation and purification, as well as to derivative compounds, and to additional aspects based on the discovery of antitumor and other activities.

BACKGROUND OF THE INVENTION

The macrolides called oligomycins and homooligomycins are known from J. Antibiotics 46: 1334~1341. 1993; J. Antibiotics 45: 171~179, 1992; and J. Antibiotics 49: 1275~1277, 1996.

OBJECTS OF THE INVENTION

New antiproliferative compounds are still needed for treatment of several human tumors, due to the fact that a high number of cancer cell lines. including those displaying MDR phenotype, are not efficiently treated by any drugs Yet another objective of this invention is to provide pharmaceutical compositions for administering to a patient in need of treatment with the active compound.

Microbial products are interesting because industrial production is well established at present times. Therefore, another objective of this invention is directed to the production of the active compound and to its isolation and purification from the resulting fermentation broth, as well the hydrolysis to an aglycone compound and derivatisation to related compounds.

SUMMARY OF THE INVENTION

This invention provides a compound with a macrolide-like structure, designated IB-96212, of the following formula,

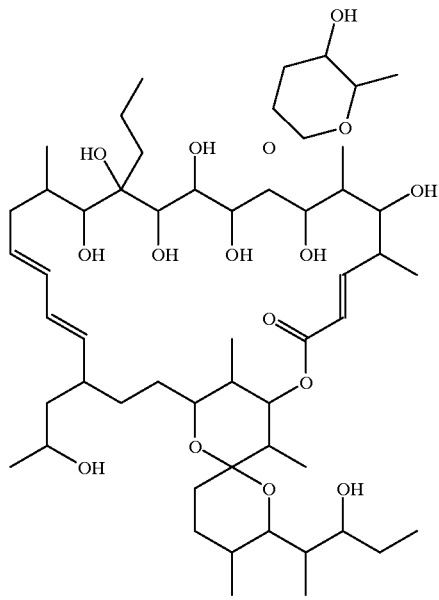

A process of obtaining IB-96212 is also provided, and the preferred process comprises cultivating a strain of a microorganism capable of producing IB-96212 in an aqueous nutrient medium with assimilable carbon and nitrogen sources and salts, under controlled submerged aerobic conditions. The resultant broth itself, either unpurified or partly purified and having antitunor activity, is also part of this invention. The compound IB-96212 can be recovered and purified from the cultured broth. The compound and the fermentation broth demonstrate interesting activity against several human cancer cells, among them sensitive and multi-drug resistant (MDR) leukaemia cells. Additionally, IB-96212 presents antibiotic activity against some Gram-positive bacteria.

From this compound IB-96212, a trideoxy sugar identified as L-rhodinose can be removed by hydrolysis, leaving the active aglycone compound IB-96212B which has the core 26-membered macrolide ring system of the parent IB96212.

Thus, the invention further provides the compound IB-96212B with the structure:

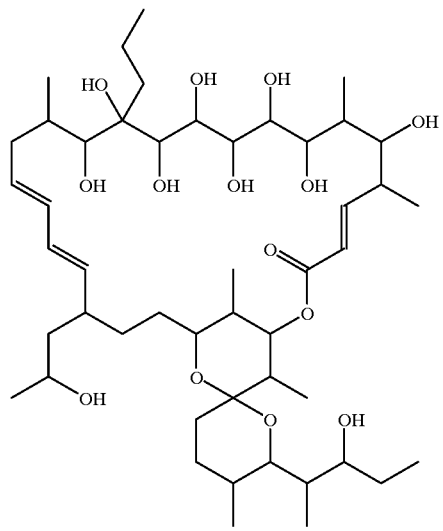

IB-96212B has activity comparable to the parent IB-96212.

In the compound IB-96212, the trideoxy sugar which we identify as L-rhodinosc can itself be derivatised or the sugar can be replaced, in either case giving further derivatives of IB-96212 having a group other than L-rhodinose at the position of the sugar. Thus, more broadly, the present invention provides a compound of the general formula:

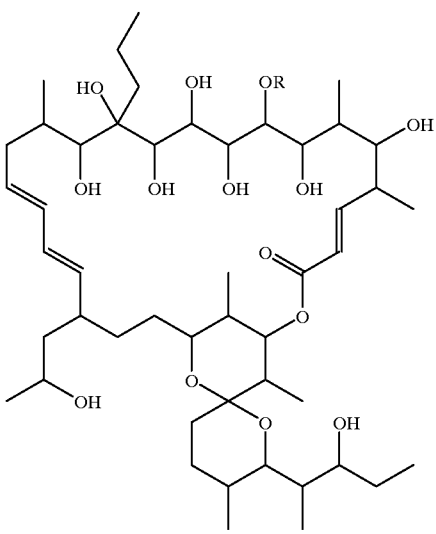

where R is hydrogen or a substituent group.

Illustratively, R is hydrogen or a group selected from a saccharide group, a hydrocarbyl group, an acyl group, a heterocyclyl group, or some other suitable substituent The nature of the substituent group is not crtical. The sacchaide group is suitably a mono-, di- or tri-saccharide which may be a deoxysaccharide. The hydrocarbyl can be alkyl, cycloalkyl, aryl, aralkyl, or alkylaryl, especially $C_1$–$C_6$ atkyl, cyclo-($C_4$–$C_8$)alkyl, phenyl, naphthyl or benzyl. The heterocyclyl group can be a 4 to 8 membered ring having 1 to 4 heteroatoms, especially a 5 or 6 membered ring having 1 or 2 hetero atoms chosen from oxygen, sulphur or nitrogen. The hydrocarbyl group, acyl group or heterocyclyl group can itself be substituted, for example with 1, 2 or 3 subsituents chosen among $C_1$–$C_6$ alkyl, $C_1$–$C_6$ alkoxy, halogen, hydroxy, amino or other groups.

The preferred culture to obtain IB-96212 is a new strain designated ES25-008, and its chemical, biochemical and morphological chambers show that it belongs to the genus Micromonospora, being taxonomically classified as Micromonospora sp.

As described above, the compounds IB-96212 and IB-96212B have been found to be effective in the inhibition of the proliferative activity of several human and murine leukaemia cell-multidrug resistant (MDR) as well as sensitive cell lines—as well as against other human tumors. It follows that other compounds of the given general formula will retain such activity.

BRIEF DESCRIPTION OF THE DRAWINGS

Figure 12:
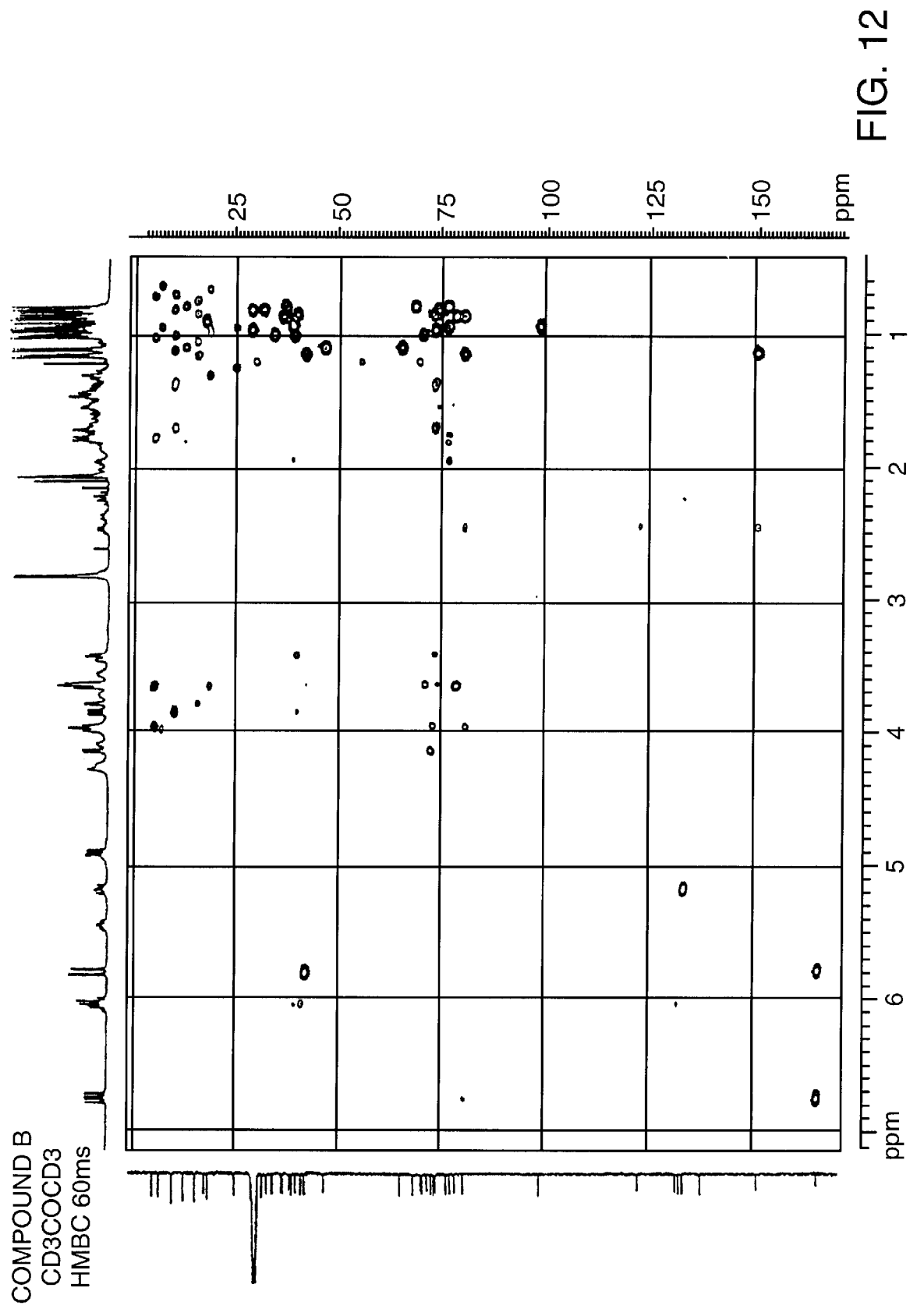

FIG. 12 is an HMBC 60 ms NMR spectrum of IB-96212B taken in acetone-$d_6$;

DETAILED DESCRIPTION OF IENVENTION

The Producing Organism

Figure 1B:
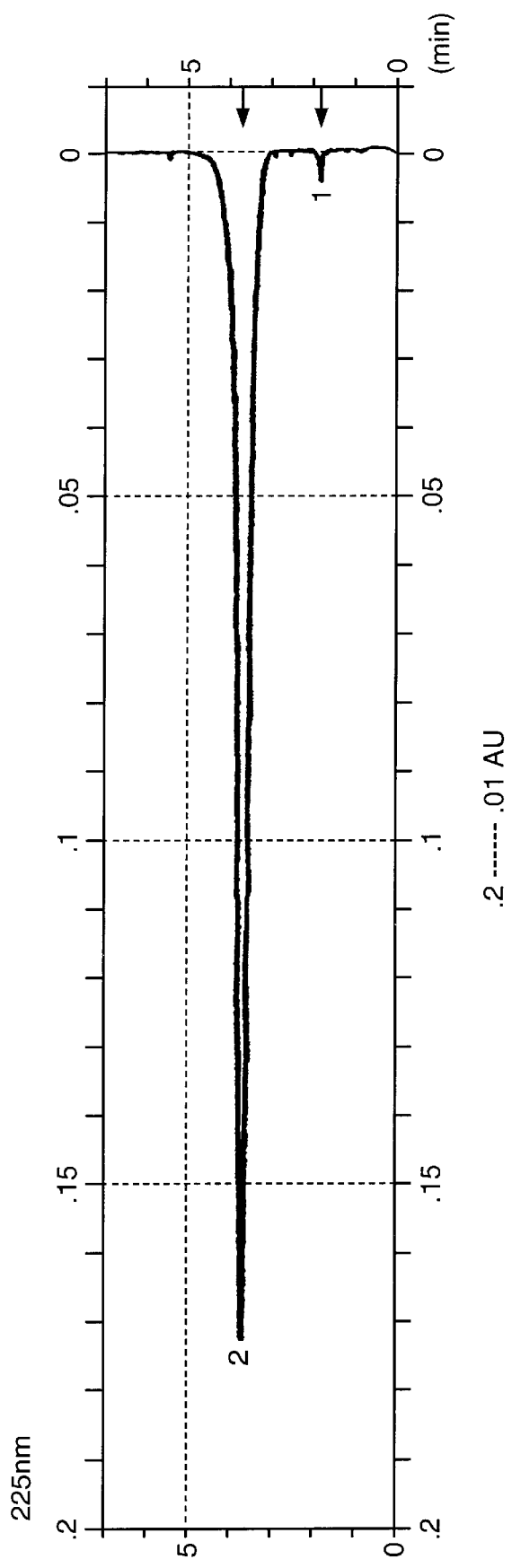
FIG. 1 is an HPLC chromatogram of purified IB-96212.

The miicro-organism utilized for the production of IB-96212 and thus for IB-96212B is preferably Micromonospora sp. strain ES25-008, a culture of which has been deposited in the Colección Española de Cultivos Tipo at the Univesity of Valencia, Spain under the accession number CECT 3333. This deposit has been made under the provisions of the Budapest Treaty, and given the deposit date of Aug. 4, 1997. The organism was isolated from an unidentified marine sponge. The taxonomic methods described herein are those reported in Table 1. All cultures were incubated at 27° C. and records of results were made weekly up to 21 days.

TABLE 1

| 1. | Media for colonial morphology studies: |
|---|---|
| | ISP Media No. 2, 3, 5 and 6: Shirling & Gotlieb, (7). |
| | ATCC Medium No. 172: ATCC Catalog. |
| | Czapek Agar Difco |
| | Bennet Agar, Waksman, (9) |
| | 1.5% Water Agar, Luedemann (5) |
| | All media were supplemented with 50% ASW |
| 2. | Physiological characteristics studies: |
| | ISP medium n° 1, Shirling and Gotlieb, (7) |
| | NaCl resistance: ATCC 172 with 0, 2, 4, 7 and 10% NaCl. |
| | Carbon utilization: ISP-9, E. B. Shirling & D. Gotlieb, (7) |
| 3. | Chemical Composition studies: |
| | Fatty acids analysis, Van der Auwera et al. (8) |
| | Whole cell sugar analysis, Guerrant and Moss. (3) |

A description of the organism is as follows:
Morphology;
After 21 days at 28° C. growth was observed in ISP2 and 172 broth supplemented with artificial sea water (ASW). Several shades of orange were observed on the different media studied. No aerial mycelium was formed. Substrate mycelium was branched. Isolated terminal spores over the substrate mycelium occur. The spores were spherical. Some overgrowth of mycelia mass can be detected in some media, and after at least 14 days of incubation.
Physiological Charcteristics:
No diffusible pigments were formed by strain ES25-008, neither on solid or liquid media. Resistance to NaCl was over 4%. Optimum growth temperature range was between 25° C and 35° C. The organism grew on glucose, sucrose, xylose and mannose as the sole carbon source, however, growth on raffinose, inositol, galactose, fructose, melibiose, ethanol, glycerol, and rhamnose was negative, and growth on mannitol was doubtful.

Cell Chemical Composition:
Aminoacids;
Meso-2,6-Diaminopimelic acid was present in the whole cell hydrolysate of strain ES25-008.
Fatty Acids:
FAME composition is as follows in Table 2:

TABLE 2

| 13:0 | i-14:0 | 14:0 | i-15:0 | n-15:0 | 15:0 | i-16:1 | i-16:0 | 16:1 | 16:0 |
|---|---|---|---|---|---|---|---|---|---|
| <1 | <1 | <1 | 8.21 | 1.00 | 1.09 | <1 | 35.07 | <1 | 1.12 |

| i-17:1 | i-17:0 | n-17:0 | 17:1 | 17:0 | i-18:1 | i-18:0 | cis-18:1 | 18:0 |
|---|---|---|---|---|---|---|---|---|
| <1 | 3.18 | 3.39 | 29.48 | 7.88 | 1.44 | <1 | 2.30 | <1 |

Sugars:
Whole cell sugar pattern showed the presence of xylose, ribose, and glucose when analyzed by gas chromatography. Arabinose was detected in trace amounts. This pattern groups this strain within the D group of Lechevalier et al.(4). Other sugars detected were mannose, galactose, m-inositol and mannosamine. The polyalcohol arabitol and muramic acid were other cellular components. Madurose was not detected.

Based on the preceding characteristics the culture has been determined as a species of the genus Micromonospora, with no similarity to any of the known type strains of this genus available in international collections. The closest resemblance by fatty acid chromatographic analysis was to *Micromonospora chalcea* ATCC 31395 with only 80% similarity.

While the deposited organism is clearly preferred, the present invention is not restricted or limited to this particular strain or organisms. It is the intention of the present inventors to include any other IB-96212 producing organisms, strains or mutants within the scope of this invention.

Fermentation:
Micromonospora sp. ES25-008 when cultured under controlled conditions in a suitable medium produces the antibiotic IB-96212. This strain is grown in an aqueous nutrient medium, under aerobic and mesophilic conditions, preferably between 24° C. and 35° C at a pH ranging between 6.0 and 8.0. A wide variety of liquid culture media can be utilized for the cultivation of the organism, useful media are those that include an assimilable carbon source, such as starch, dextrin, sugar molasses, glycerol, glucose, sucrose, and the like, an assimilable nitrogen source such as proteins, protein hydrolysates, defatted meals, corn steep, and the like, and useful inorganic anions and cations such as sodium, magnesium. potassium, ammonium, sulfate, chloride, phosphate, carbonate, and the like. Trace elements may be added also. Aeration is preferably achieved by supplying air to the fermentation medium. Agitation is provided by a mechanical impeller. Conventional fermentation tanks have been found to be well suited for carrying out the cultivation of this organism. The addition of nutrients and pH control as well as antifoaming agents during the different stages of fermentation mnay be needed for increasing production and avoid foaming.

The required steps needed for the production of IB-96212 by the preferred organism are:

Start with frozen or lyophilized mycelium. Obtain mycelial mass culturing the initial cells in shake flasks with a culture medium containing some of the ingredients described above at mesophilic temperatures and in aerobic conditions, this step may be repeated several times as needed and the material collected will be used as an inoculum to seed one or several fermentation tanks with appropriate culture medium, if desired these tanks can be utilized also as inoculum, and this step can be repeated several times when needed, or they can serve as the production stage, depending on the broth volume needed. Sometimes the production medium may be different than that used as inoculum.

In Table 3 typical media are described that can be used for inoculum development and production of IB-96212:

TABLE 3

| Inoculum medium | | Production medium | |
|---|---|---|---|
| Glucose | 5 g | Glucose | 5 g |
| Starch | 20 g | Starch | 20 g |
| Beef extract | 3 g | Soybean meal | 15 g |
| Yeast extract | 5 g | Yeast extract | 5 g |
| Tryptone | 5 g | Tryptone | 2 g |
| $CaCO_3$ | 4 g | $CaCO_3$ | 4 g |
| NaCl | 4 g | NaCl | 4 g |
| $Na_2SO_4$ | 1 g | $Na_2SO_4$ | 1 g |
| KCl | 0.5 g | KCl | 0.5 g |
| $MgCl_2$ | 2 g | $MgCl_2$ | 2 g |
| $K_2HPO_4$ | 0.5 g | $K_2HPO_4$ | 0.5 g |
| Tap water to | 1,000 ml | Tap water to | 1,000 ml |

Production of IB-96212 can be monitored by whole broth assay against the Cell line murine leukaemia P-388 or by HPLC

ISOLATON OF IB-96212

Antibiotic IB-96212 can be isolated from the mycelia cake by extraction with a suitable mixture of solvent such as $CHCl_3:CH_3OH:H_2O$. The activity is concentrated in the lower layer. The extracts froin two repeated extraction can be combined and evaporated to dryness in vacuo.

Separation and purification of IB-96212 from the crude active extract can be performed by the use of the proper combination of conventional chromatographic techniques.

Fractionation can be guided by the antiwamor activity of fractions, or by TLC visualized with vanillin in conc. $H_2SO_4$ or analytical HPLC with diode aray detector. HPLC analysis are performed at room temperature (Waters RCM 8×10, 8C18 10 cartridge) using as mobile phase methanol:water 92:8 and a flow rate of 2 mm/min, and plotted at 225 nm. In these conditions IB-96212 retention time is 3.64 min as shown in FIG. 1.

On the basis of detailed analysis of their various spectral characteristics, the pure compound can be identified as IB-96212 (see data reproduced in FIGS. 2 to 6).

Figure 2A:
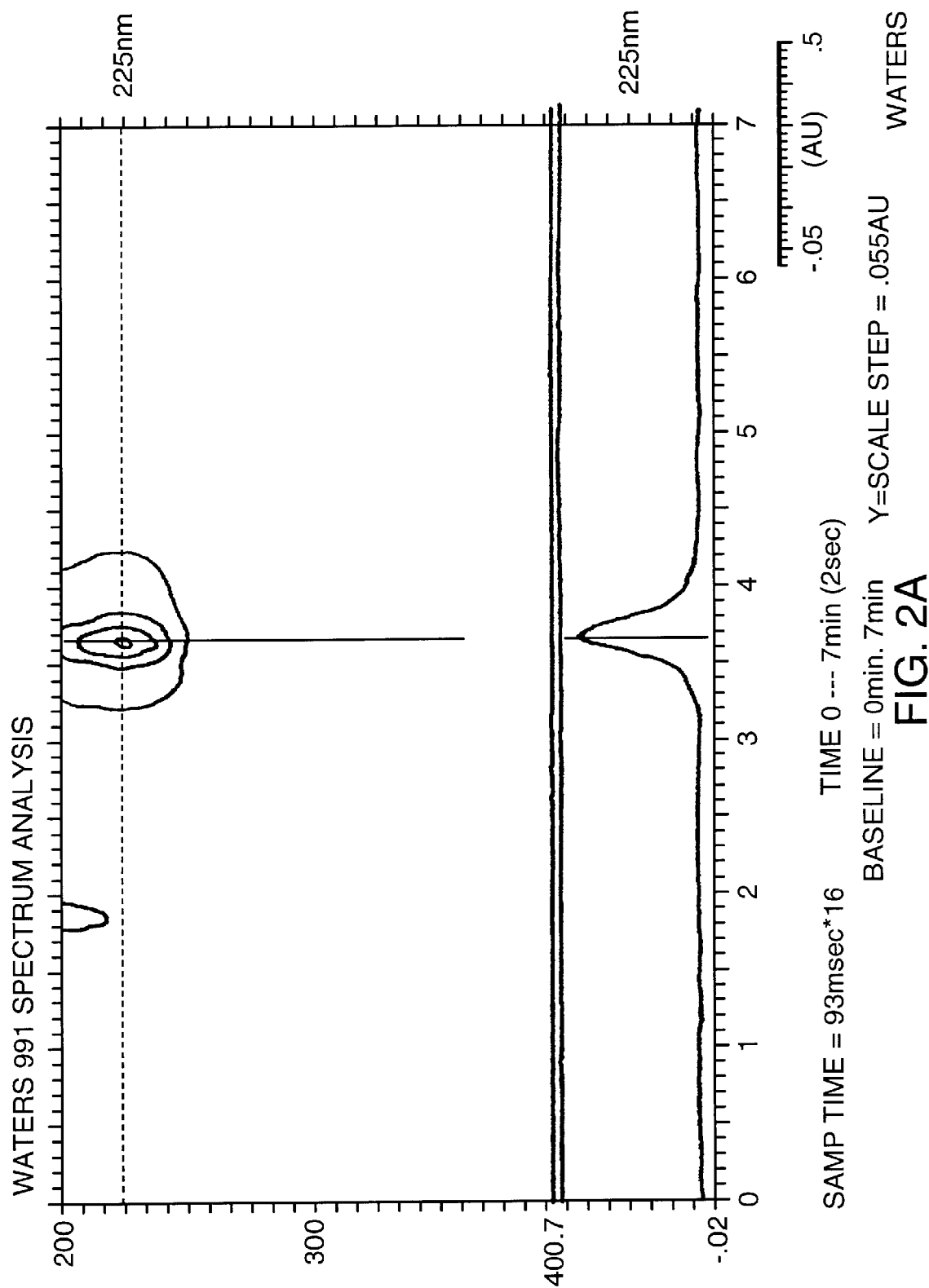
FIG. 2 is an ultraviolet spectrum (UV) of purified IB96212.
Figure 2B:
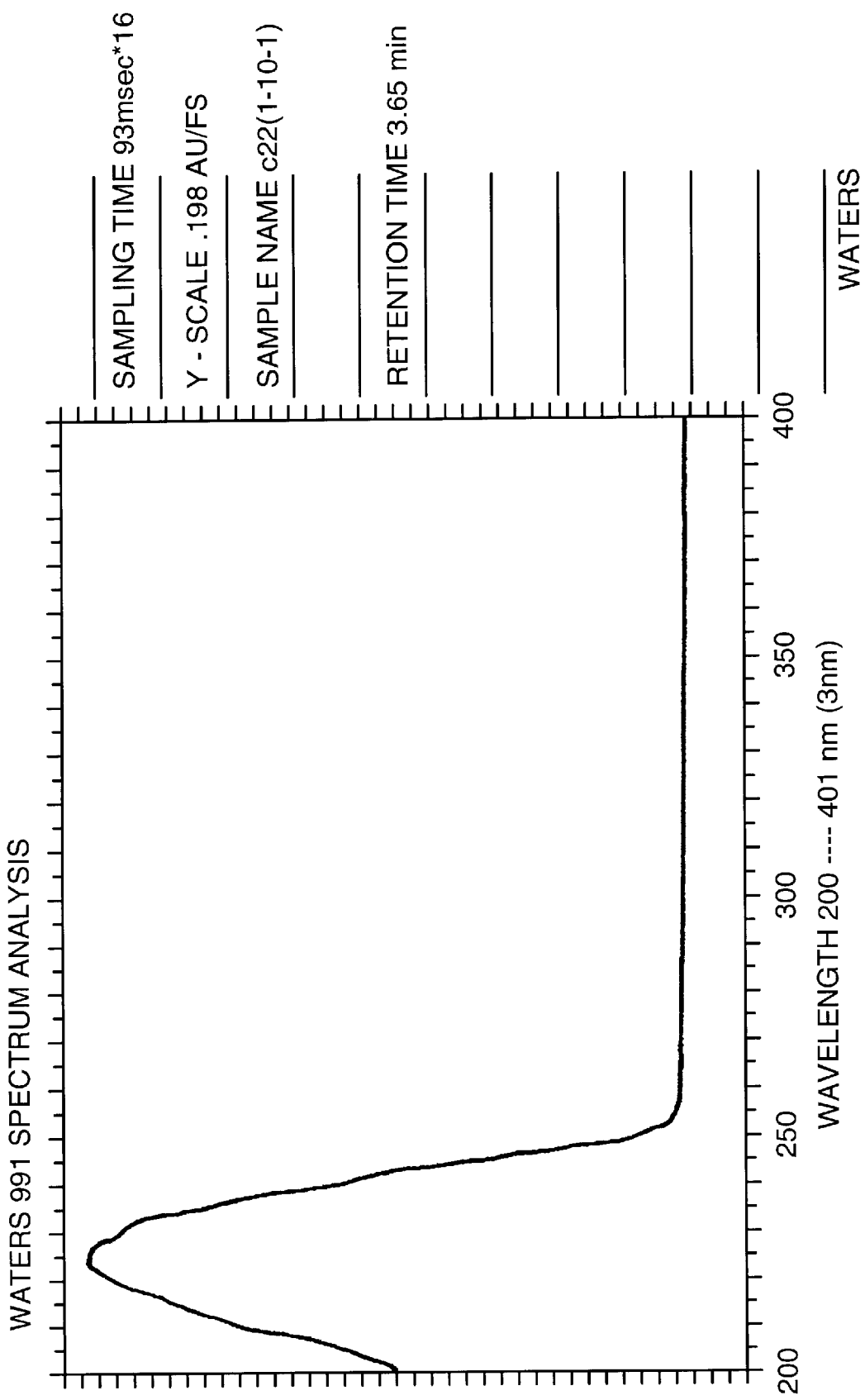

The U.V. spectrum shows absorption at 225 mn as reported in FIG. 2.

Figure 3:
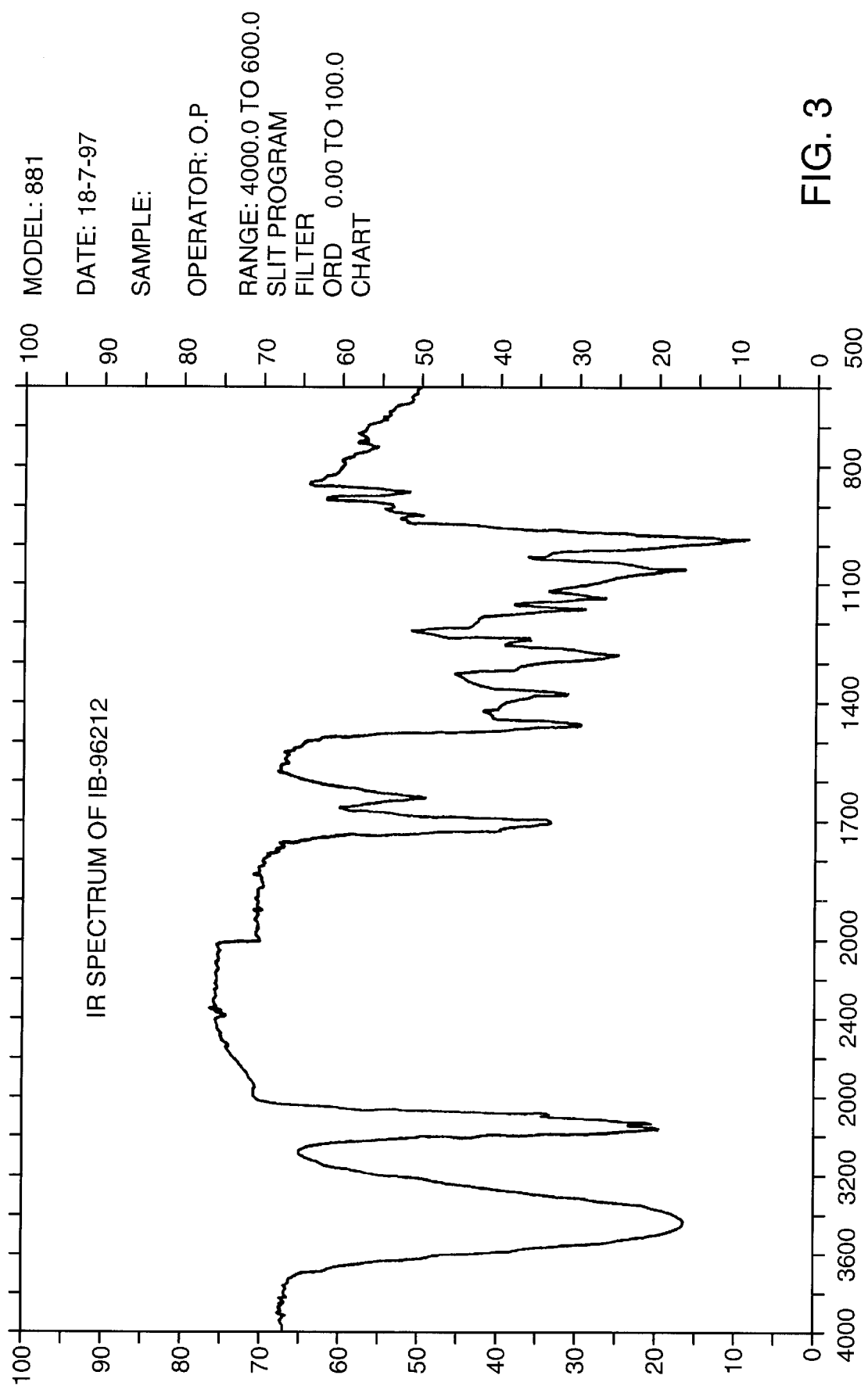
FIG. 3 is an infrared (IR) spectrum of purified IB-96212.

The infrared absorption spectrum in KBr is shown in FIG. 3 of the accompanying drawings.

Figure 4:
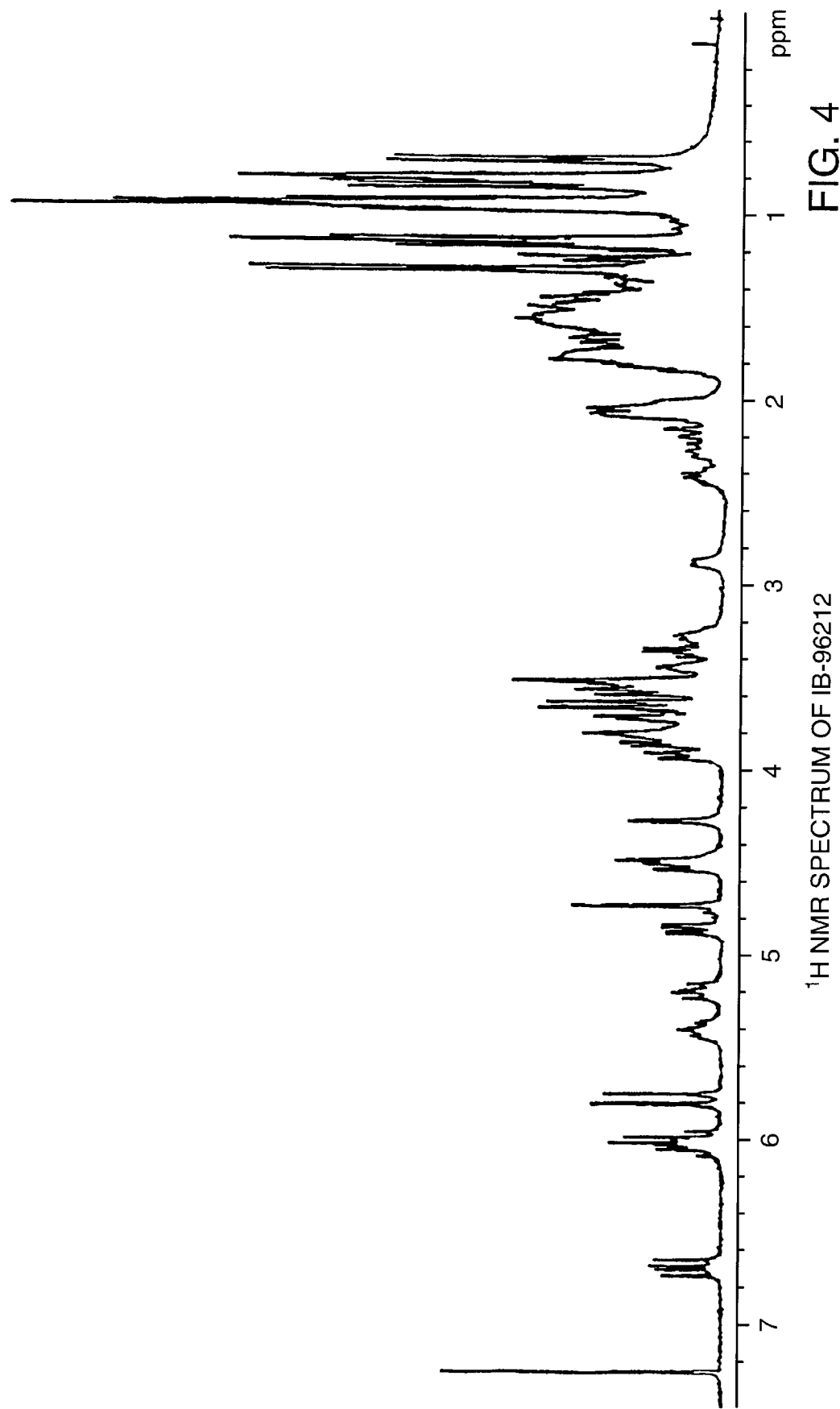
FIG. 4 is a proton NMR (1H) spectrum of purified IB-96212.
Figure 5:
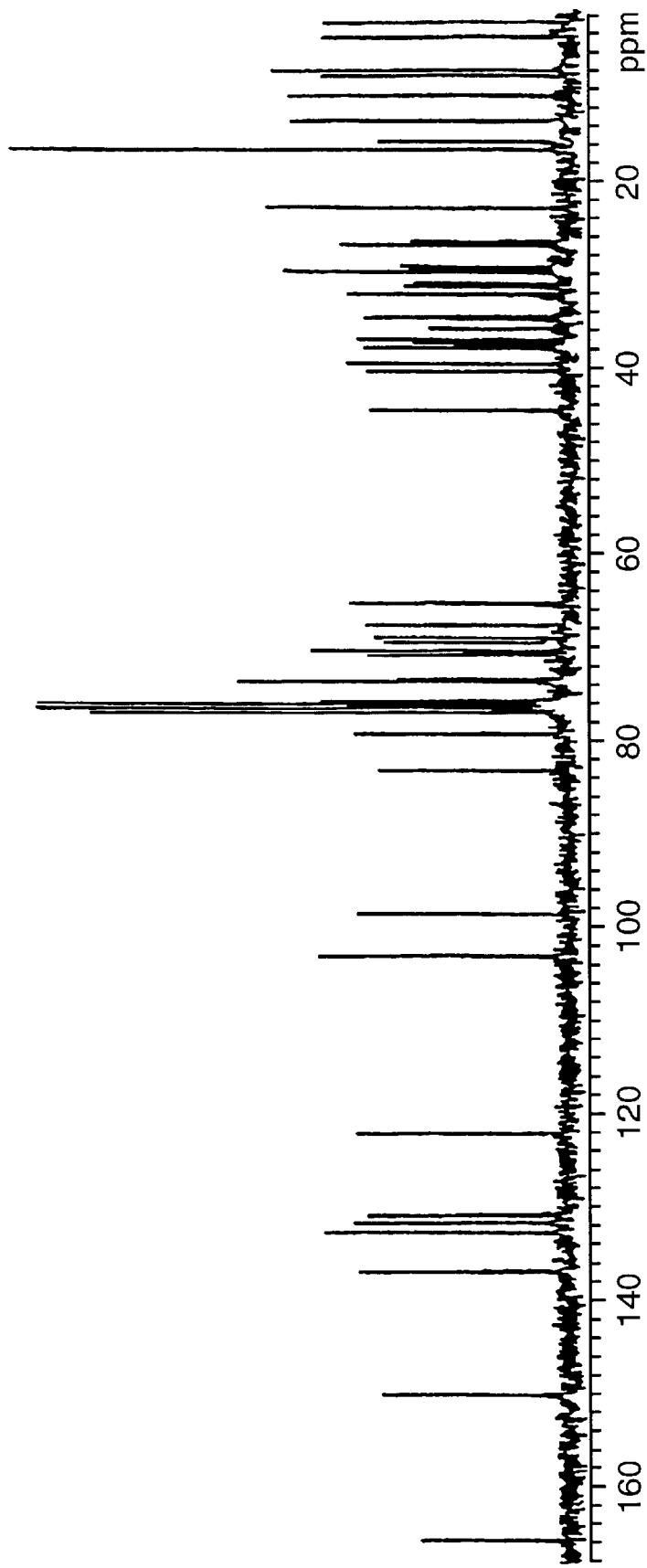
FIG. 5 is a carbon-13 NMR (13C) spectrume of purified B-96212.

The 1H and 13C N.M.R. spectra are reported in FIG. 4 and FIG. 5 respectively.

Figure 6A:
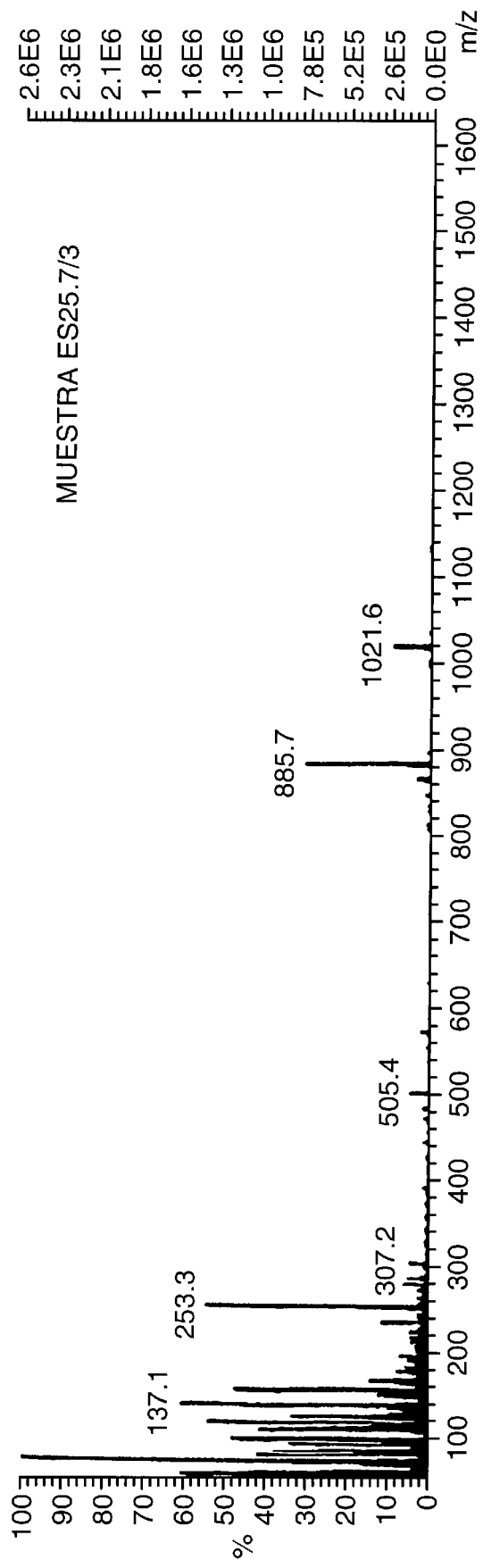
FIG. 6 is a mass spectrum of purified IB-96212.
Figure 6B:
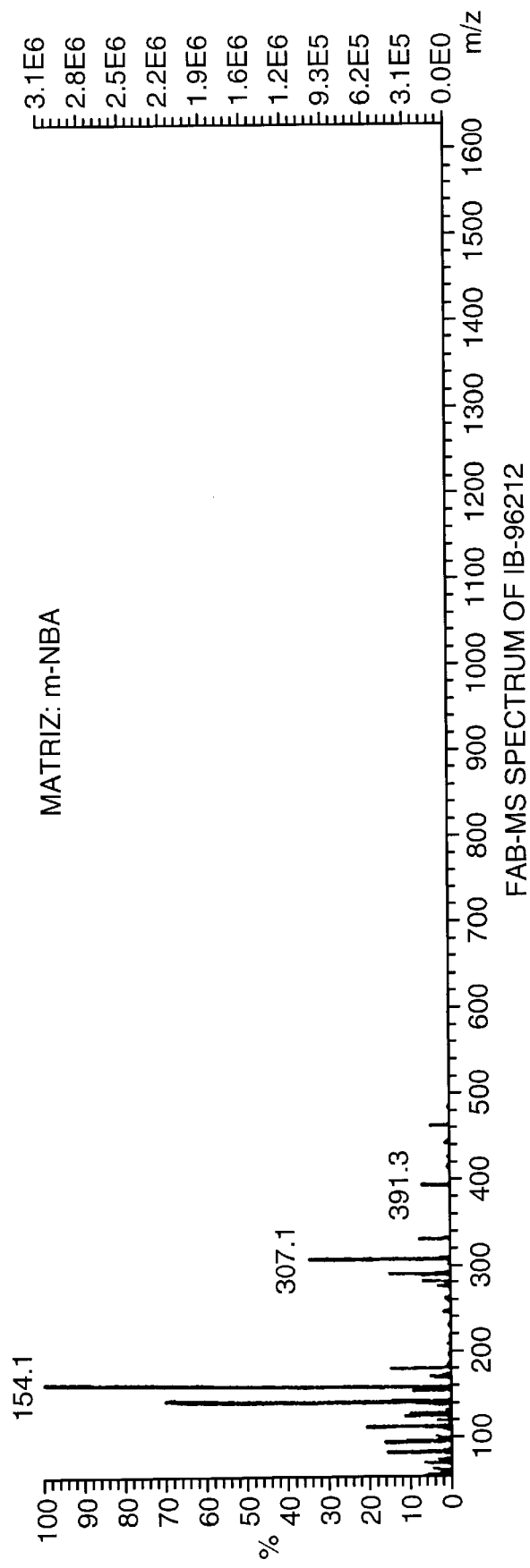
Figure 7:
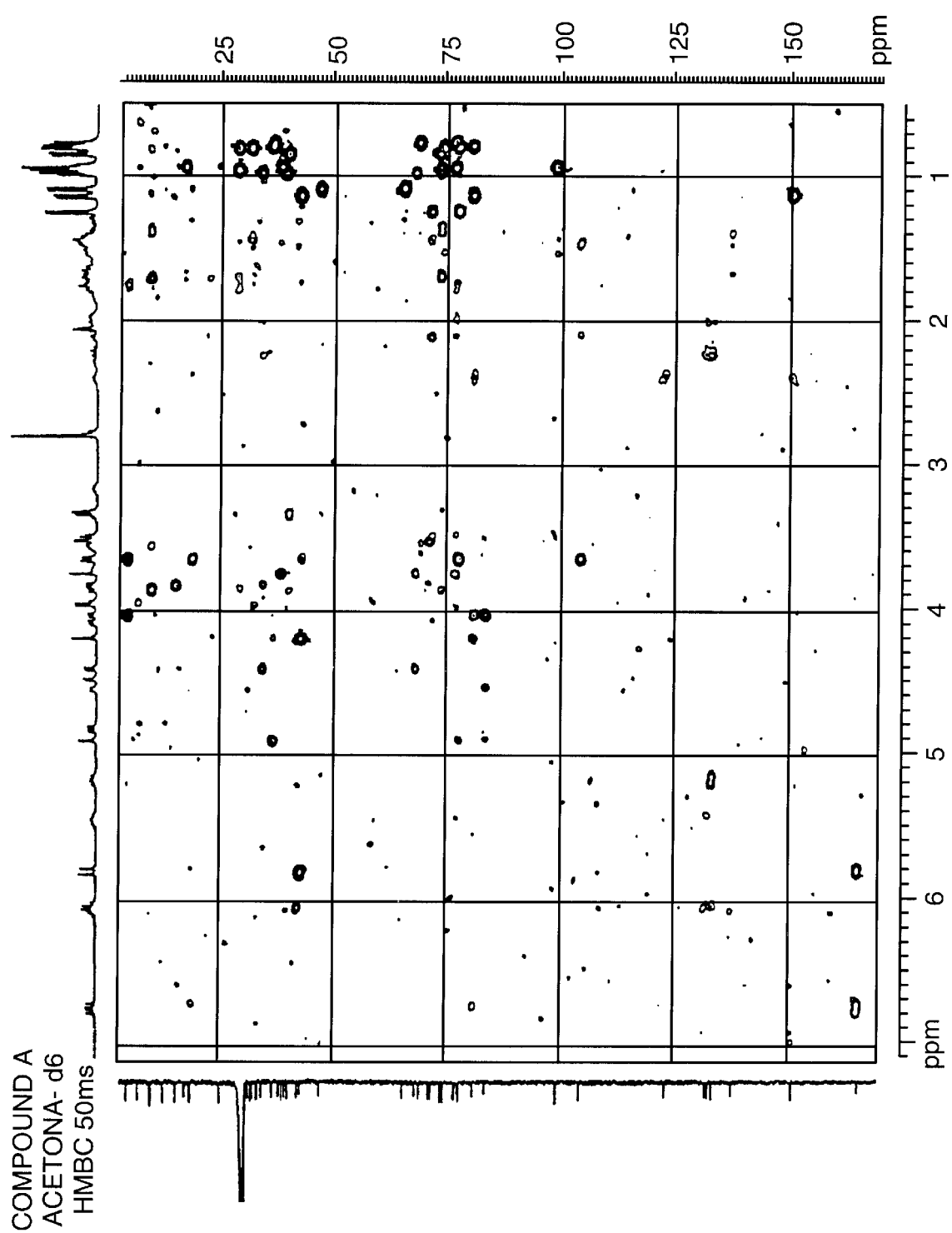
FIG. 7 is an HMBC NMR spectrum of IB-96212 taken in acetone-$d_6$.
Figure 8:
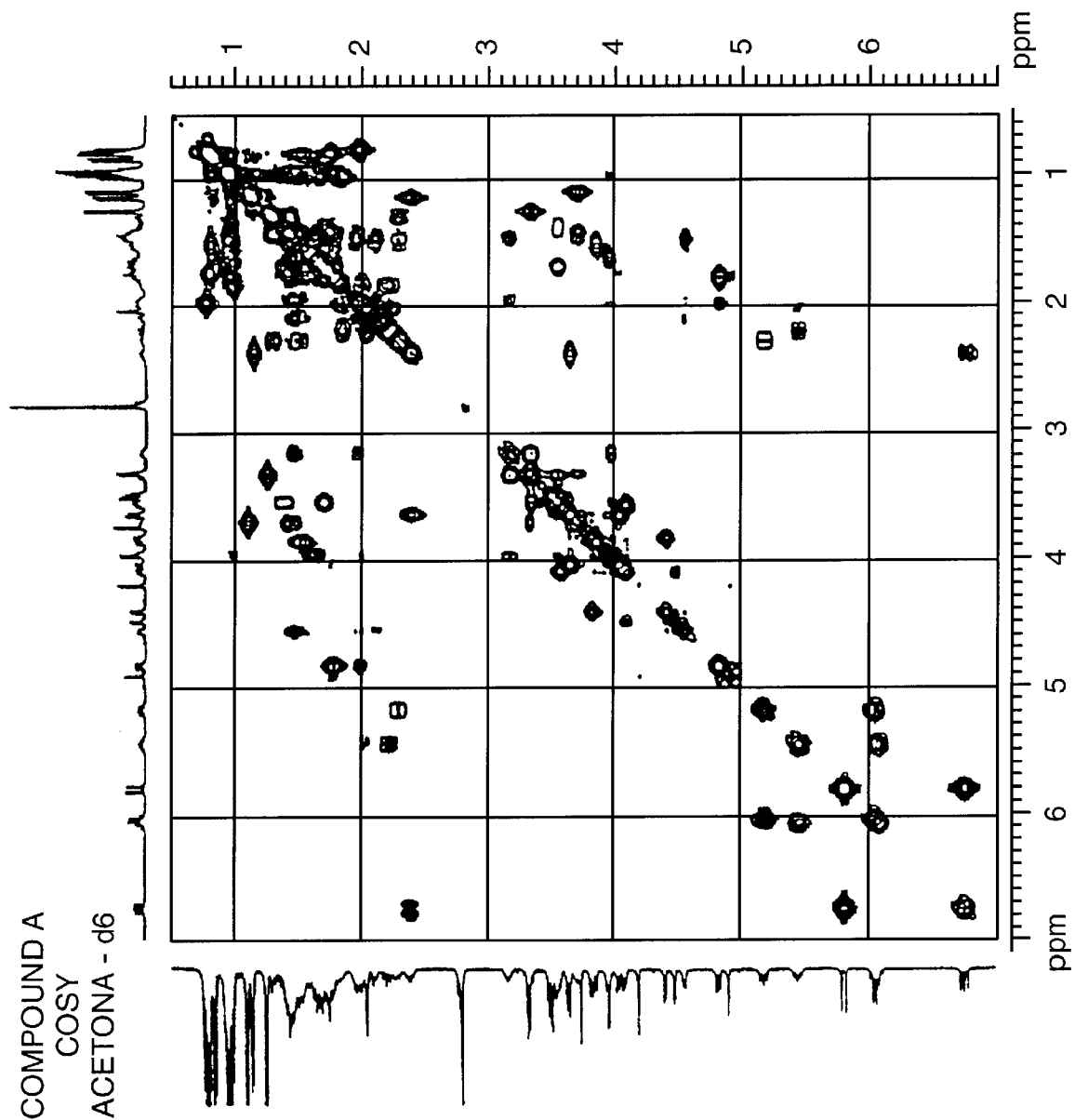
FIG. 8 is a COSY NMR spectun of IB-96212 taken in acetone-$d_6$.
Figure 9:
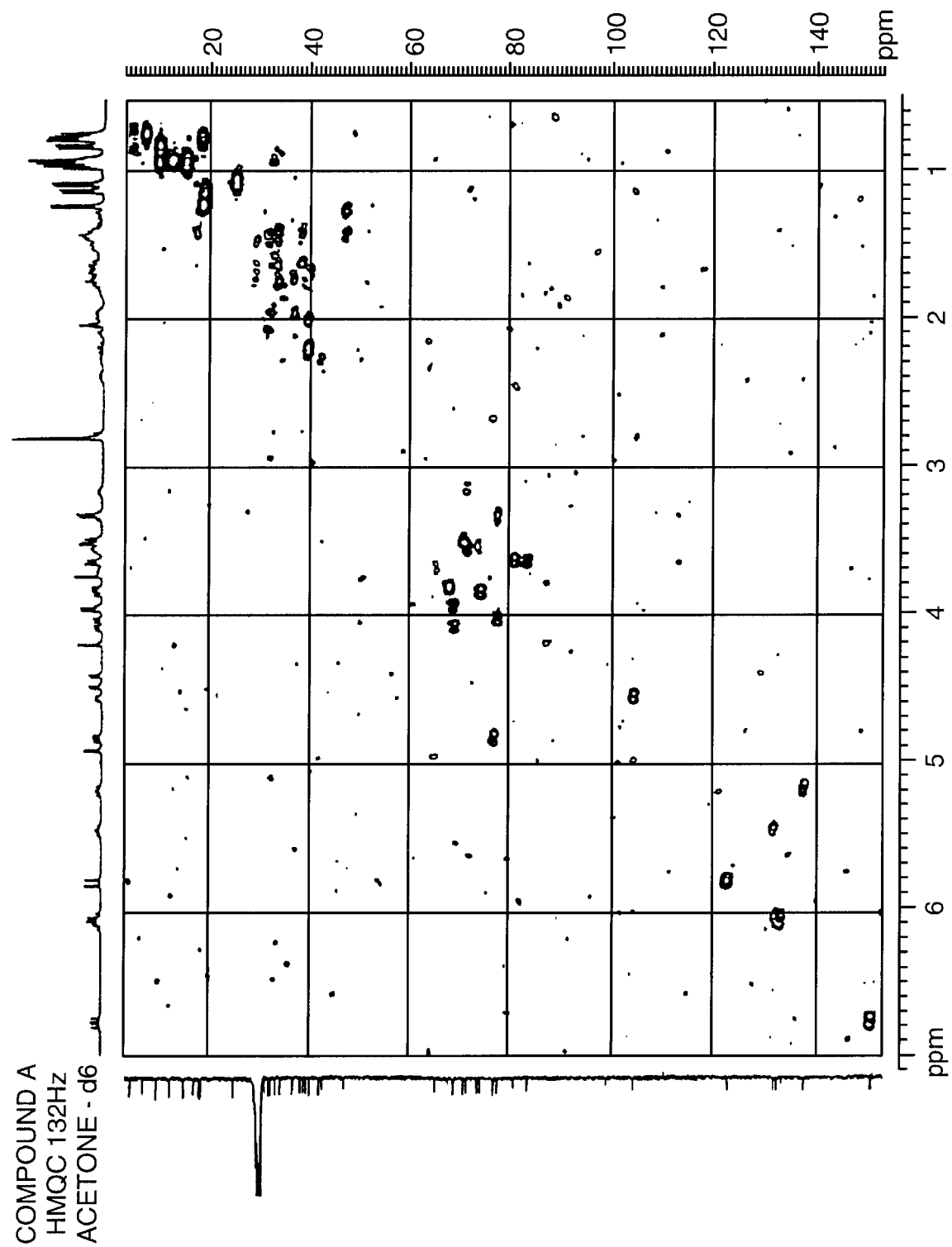
FIG. 9 is an HMQC 132 Hz NMR specinum of IB-96212 taken in acetone-$d_6$.

The FAB-MS spectrum displayed a $(M+Na)^-$ peak at 1021, is reported in FIG. 6.

The $^1H$ NMR data for B-96212 are tabulated as follows:

| position | $\delta_H$ [int mult, J (Hz)] |
|---|---|
| 1 | |
| 2 | 5.80 (1H, d, 15.5) |
| 3 | 6.74 (1H, dd, 10.5, 15.5) |
| 4 | 2.37 (1H, dt, 6.5, 10.0) |
| 5 | 3.62 (1H, d, 9.0) |

-continued

| position | $\delta_H$ [int mult, J (Hz)] |
|---|---|
| 6 | 1.73 (1H, m) |
| 7 | 4.02 (1H, d, 9.0) |
| 8 | 3.62 (1H, d, 9.0) |
| 9 | 3.54 (1H) |
| 10 | 4.07 (1H, dd, 4.5, 8.05) |
| 11 | 3.46 (1H) |
| 12 | |
| 13 | 3.78 (1H, dd, 1.5, 6.5) |
| 14 | 1.82 (1H, m) |
| 15 | 1.98 (1H, m) |
| | 2.19 (1H, m) |
| 16 | 5.42 (1H, ddd, 3.5, 10.5, 14.5) |
| 17 | 6.03 (1H, dd, 10.5, 14.5) |
| 18 | 6.01 (1H, dd, 10.5, 14.5) |
| 19 | 5.16 (1H, dd, 10.0, 14.5) |
| 20 | 2.26 (1H, dt, 10.0) |
| 21 | 1.40 (1H, m) |
| | 1.64 (1H, m) |
| 22 | 0.92 (1H, m) |
| | 1.58 (1H, m) |
| 23 | 3.92 (1H, d, 10.5) |
| 24 | 1.95 (1H, m) |
| 25 | 4.81 (1H, dd, 5.0, 11.5) |
| 26 | 1.75 (1H) |
| 27 | |
| 28 | 1.40 (1H, m) |
| | 1.75 (1H, m) |
| 29 | 1.49 (1H, m) |
| | 1.65 (1H, m) |
| 30 | 1.49 (1H, m) |
| 31 | 3.82 (1H, d, 10.5) |
| 32 | 1.66 (1H, m) |
| 33 | 3.52 (1H) |
| 34 | 1.35 (1H m) |
| | 1.68 (1H, m) |
| 35 | 0.94 (3H, t, 7.5) |
| 36 | 1.13 (3H, d, 6.5) |
| 37 | 0 77 (3H, d, 7.0) |
| 38 | 1.40 (1H, m) |
| | 1.64 (1H, m) |
| 39 | 1.42 (1H, m) |
| | 1.54 (1H, m) |
| 40 | 0.91 (3H, t, 7.0) |
| 41 | 0.96 (3H, d, 6.5) |
| 42 | 1.25 (1H, m) |
| | 1.42 (1H, m) |
| 43 | 3.68 (1H, m) |
| 44 | 1.08 (3H, d, 6.5) |
| 45 | 0.75 (3H, d, 7.0) |
| 46 | 0.92 (3H, d, 7.0) |
| 47 | 0.78 (3H, d, 6.0) |
| 48 | 0.82 (3H, d, 7.0) |
| 5-OH | 4.21 (1H, s) |
| 7-OH | 4.90 (1H, s) |
| 9-OH | 3.50 (1H, s) |
| 10-OH | 4.50 (1H, d, 4.5) |
| 11-OH | 3.53 (1H, s) |
| 12-OH | 3.75 (1H, s) |
| 13-OH | 4.43 (1H, d, 6.5) |
| 33-OH | 3.38 (1H, d, 6.0) |
| 43-OH | 3.39 (1H, d, 6.0) |
| 1' | 4.54 (1H, dd, 1.5, 7.7) |
| 2' | 1.43 (1H, m) |
| | 2.09 (1H, dt, 2.0, 8.5) |
| 3' | 1.46 (1H, m) |
| | 1.93 (1H, m) |
| 4' | 3.15 (1H, sep, 5.0) |
| 5' | 3 31 (1H, dq, 2.5, 6.0) |
| 6' | 1.24 (3H, d, 6.0) |
| 4'-OH | 4.04 (1H, d, 5.0) |

The $^1$H NMR data for IB-96212B are tabulated as follows:

| position | $\delta_H$ [int mult, J (Hz)] |
|---|---|
| 1 | |
| 2 | 5.80 (1H, d, 15.5) |
| 3 | 6.75 (1H, dd, 10.0, 15.5) |
| 4 | 2.45 (1H, dt, 6.5, 10.0) |
| 5 | 3.65 (1H) |
| 6 | 1.75 (1H, m) |
| 7 | 3.94 (1H, d, 8.0) |
| 8 | 3.62 (1H) |
| 9 | 3.63 (1H) |
| 10 | 4.14 (1H, d, 6.5) |
| 11 | 3.50 (1H) |
| 12 | |
| 13 | 3.78 (1H, broad s) |
| 14 | 1.85 (1H, m) |
| 15 | 2.10 (1H, m) |
| | 2.22 (1H, m) |
| 16 | 5.45 (1H, ddd, 3.5, 10.5, 14.5) |
| 17 | 6.01 (1H, dd, 10.0, 14.5) |
| 18 | 6.08 (1H, dd, 10.0, 14.5) |
| 19 | 5.18 (1H, dd, 10.5, 14.5) |
| 20 | 2.35 (1H, dt, 10.0) |
| 21 | 1.46 (1H, m) |
| | 1.65 (1H, m) |
| 22 | 1.02 (1H, m) |
| | 1.60 (1H, m) |
| 23 | 3.96 (1H, d, 10.5) |
| 24 | 1.93 (1H, m) |
| 25 | 4.90 (1H, dd, 5.5, 11.5) |
| 26 | 1.75 (1H) |
| 27 | |
| 28 | 1.40 (1H, m) |
| | 1.77 (1H, m) |
| 29 | 1.50 (1H, m) |
| | 1.65 (1H, m) |
| 30 | 1.52 (1H, m) |
| 31 | 3.84 (1H, d, 10.0) |
| 32 | 1.68 (1H, m) |
| 33 | 3.55 (1H, m) |
| 34 | 1.37 (1H, m) |
| | 1.70 (1H, m) |
| 35 | 0.95 (3H, t, 7.5) |
| 36 | 1.14 (3H, d, 6.5) |
| 37 | 0.85 (3H, d, 7.0) |
| 38 | 1.45 (1H, m) |
| | 1.59 (1H, m) |
| 39 | 1.35 (1H, m) |
| | 1.55 (1H, m) |
| 40 | 0.88 (3H, t, 7.0) |
| 41 | 0.98 (3H, d, 6.5) |
| 42 | 1.25 (1H, m) |
| | 14.5 (1H, m) |
| 43 | 3.80 (1H, m) |
| 44 | 1.08 (3H) |
| 45 | 0.78 (3H, d, 7.0) |
| 46 | 0.93 (3H, d, 7.0) |
| 47 | 0.80 (3H, d, 6.0) |
| 48 | 0.83 (3H, d, 7.0) |
| 5-OH | |
| 7-OH | |
| 9-OH | |
| 10-OH | |
| 11-OH | |
| 12-OH | |
| 13-OH | 4.24 (1H, broad s) |
| 33OH | 3.40 (1H, d, 6.4) |
| 43OH | 3.43 (1H, d) |
| 1' | |
| 2' | |
| 3' | |
| 4' | |
| 5' | |
| 6' | |
| 4'-OH | |

The $^{13}$C NMR data for IB-9212 and IB-96212B are tabulated as follows;

| position | IB-96212 $\delta_c$ | IB-96212B $\delta_c$ |
|---|---|---|
| 1 | 165.2 | 165.3 |
| 2 | 122.7 | 122.5 |
| 3 | 150.7 | 150.7 |
| 4 | 42.5 | 42.0 |
| 5 | 80.8 | 80.6 |
| 6 | 36.4 | 36.5 |
| 7 | 77.5 | 78.6 |
| 8 | 83.5 | 74.0 |
| 9 | 71.6 | 73.0 |
| 10 | 69.1 | 71.0 |
| 11 | 70.9 | 72.1 |
| 12 | 76.7 | 77.5 |
| 13 | 68.0 | 70.6 |
| 14 | 34.0 | 34.3 |
| 15 | 39.2 | 39.2 |
| 16 | 131.6 | 131.5 |
| 17 | 133.1 | 133.2 |
| 18 | 132.1 | 132.3 |
| 19 | 137.5 | 137.5 |
| 20 | 41.8 | 41.2 |
| 21 | 33.1 | 33.1 |
| 22 | 32.2 | 31.7 |
| 23 | 68.9 | 68.7 |
| 24 | 36.7 | 37.0 |
| 25 | 76.7 | 76.6 |
| 26 | 38.7 | 38.8 |
| 27 | 99.1 | 99.1 |
| 28 | 33.1 | 32.8 |
| 29 | 28.8 | 28.8 |
| 30 | 31.7 | 31.7 |
| 31 | 74.1 | 74.2 |
| 32 | 39.9 | 39.9 |
| 33 | 73.6 | 73.6 |
| 34 | 28.8 | 28.8 |
| 35 | 9.7 | 9.7 |
| 36 | 18.4 | 18.2 |
| 37 | 4.5 | 4.9 |
| 38 | 38.0 | 38.4 |
| 39 | 17.2 | 17.2 |
| 40 | 15.2 | 15.2 |
| 41 | 15.0 | 15.1 |
| 42 | 46.9 | 46.7 |
| 43 | 65.3 | 65.4 |
| 44 | 24.8 | 24.8 |
| 45 | 6.7 | 6.5 |
| 46 | 12.4 | 12.3 |
| 47 | 18.2 | 18.1 |
| 48 | 9.8 | |
| 1' | 104.4 | |
| 2' | 31.0 | |
| 3' | 31.9 | |
| 4' | 71.4 | |
| 5' | 77.6 | |
| 6' | 18.7 | |

Initially on the basis of the data in FIGS. 1 to 6, we assigned the structure shown in our piority GB patent filing, but with the benefit of the additional data of the later Figures for both IB-96212 and IB-96212B, we arrived at the structure of IB96212 as follows:

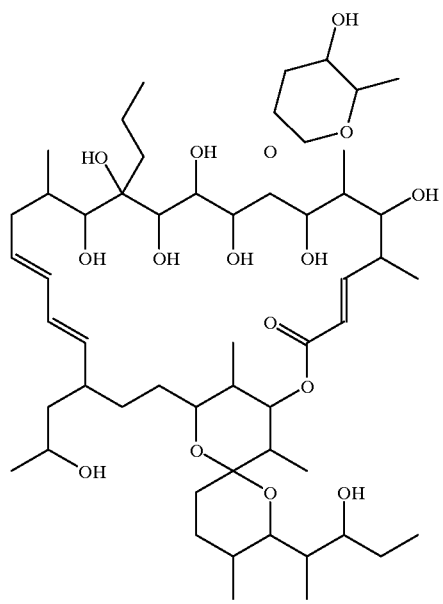

The sugar substituent can be removed by hydrolysis to leave the compound IB-96212B, of formula:

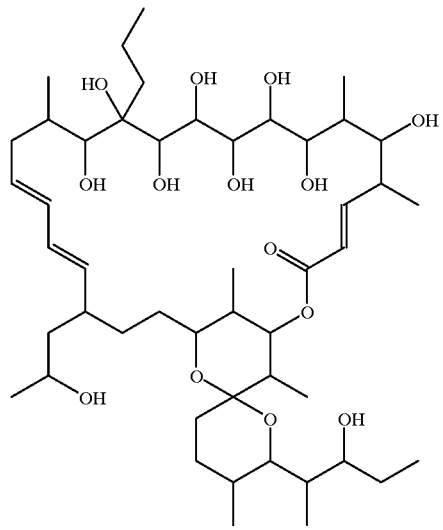

The sugar on IB-96212 can be derivatised in conventional manner, or the IB-96212B can be derivatised in conventional manner to replace the sugar with another substituent group, thereby giving a compound of the formula:

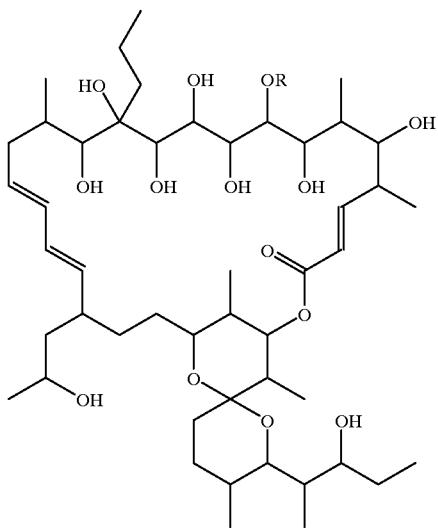

where R can be varied as desired.

BIOLOGICAL ACTITY

The compound IB-96212 shows good antibacterial activity against *Micromonospora lutens* and some activity against *Staphylococus aureus* and *Bacillus subtilis* but at higher concentrations. The antimicrobial activity of compound IB-96212 was studied incubating selected strains with different concentrations of IB-96212 in liquid Mueller-Hinton medium at 35° C.

IB-96212 and IB-96212B display good antitumor actvity against several mammalian cancer cell lines. The antitumor activity has been deteced in vitro by culturing the tumor cells following the methodology described by Bergeron, et al.(2), and by Schroeder, et al. (6). Activity against several human tumors as leukaemia, colon carcinoma, NSC lung carcinoma, melanoma, and the like has been observed.

Some tumors were more sensitive than others. As for example it was found that leukaemia cells and MDR leukaemia cells were at least 100 times more sensitive that colon carcinoma.

Activity in vivo was also assessed in groups of female mice with P388, by injection QD 1–5 ip, giving the following results shown in Table 4.

may contain the pure compound or compositions may need to be sterile when administered parenterally.

The correct dosage of a pharmaceutical composition of IB-96212, IB-96212B or derivative will vary according to the particular formulation, the mode of application, and the particular situs, host and tumor being treated. Other factors like age, body weight, sex, diet, time of administration, rate of excretion, condition of the host, drug combinations, reaction sensitivities and severity of the disease shall be taken in account. Administration can be carried out continuously or periodically within the maximum tolerated dose.

EXAMPLES OF THE INVENTION

The present invention will be further illustrated with reference to the following examples which aid in the understanding of the present invention, but which are not to be construed as limitations thereof. All percentages reported herein unless otherwise specified. are presented by weight. All temperatures are expressed in degrees Celsius. All incubations are carried out at 28° C. and flasks are shaken in an orbital shaker. All media and recipients are sterile and all culture processes aseptic.

Example 1

Stock Culture: Whole broth of a pure culture of Micromonospora sp. ES25-008 is preserved frozen in 20% glycerol.

Inoculum: A frozen culture or a well grown slant culture (5% vol.) is used to seed 100 ml of seed medium described previously contained in a 250 cc shake flask. The flask is incubated during 48 hr. 500 ml of the same medium in 2 L Erlenmeyer flask are seeded with 10% of the first stage inoculum. The flask is incubated during 48 hr.

Fermentation: With 2.5 L of second stage inoculum seed 50 L of production medium already described in a 17 L fermentation tank. The fermentation is carried out during 96 hours with 400 rpm agitation and an air flow of 0.5 V/V.M. Monitor secondary metabolite production by assay of whole broth against P-388 or by HPLC.

Example 2

Isolation: 10 L of whole harvested broth were filtrated to separate the biomass and other solids. The mycelia cake was extracted twice with a mixture solvent (2.4 L) of $CHCl_3$:$CH_3OH$:$H_2O$ (2:1:1), the activity was concentrated in the lower layer. The organic solvent was concentrated and evaporated to dryness in vacuo to yield 450 mg of crude extract.

TABLE 4

| | dose mg/kg | | body weight | | weight | day of | survival |
|---|---|---|---|---|---|---|---|
| | inject | total | day 0 | day 5 | change | death | time |
| IB-96212 | 0.02 | .1 | 21.6 ± 0.5 | 22.6 ± 0.5 | 0.8 | 2, 6, 10, 10, 13 | 8.2 ± 3.8 |
| IB-96212 | 0.01 | .05 | 20.6 ± 1.0 | 21.7 ± 0.7 | 1.1 | 9, 11, 13, 13, 14 | 12.0 ± 1.8 |
| IB-96212 | 0.005 | .025 | 22.0 ± 1.2 | 22.9 ± 0.6 | 0.8 | 10, 10, 11, 11, 13 | 11.0 ± 1.1 |
| POS | | | 21.0 ± 1.2 | 21.4 ± 1.1 | 0.5 | 8, 8, 8, 8, 8, 9, 9, 9 | 8.4 ± 0.5 |

The present invention also relates to pharmaceutical preparations which contain as active ingredient compound IB-96212 or IB-96212B or another derivative of the given general formula, as well as the processes for their preparation.

Examples of pharmaceutical compositions include any solid (tablets, pills, capsules, granules, etc.) or liquid (solutions suspensions or emulsions) with suitable composition for oral, topical or parenteral administration, and they The extract was chromatographed on silica gel using a mixture of hexane/ethyl acetate as the eluting solvent. 44 mg of a fraction with antitumor activity were eluted with hexane/ethyl acetate 30:70. Further purification was achieved by column chromatography on silica gel and the activity was eluted with chloroform/methanol 92:8 to yield 19 mg of dry matter. The last purification was carried out by column chromatography on C18 reversed phase using methanol/water 90:10 as the eluting solvent to yield 12 mg of pure IB-96212.

Example 3

Hydrolysis to IB-96212B: 31 mg of IB-96212 were dissolved in 3 ml of $CHCl_3:CH_3OH$ 1:1 and added to 10 ml of a 15% solution of $H_2SO_4$, and kept at reflux for 3 hours. The reaction mixture was diluted with 15 ml of water and extracted twice with 25 ml of CHCl3, to obtain 30 mg of reaction product, which was analysed by chromatography on silica gel and eluted with $CHCl_3:CH_3OH$ 96:4. 20 mg of the aglycone was obtained as product of the hydrolysis.

Example 4

Biological activity: the antitumor cells employed have been P-388 (suspension culture of a lymphoid neoplasm from DBA/2 mouse), A-549 (monolayer culture of a human macrocytic lung carcinoma, HT-29 (monolayer culture of a human colon carcinoma), and MEL-28 (monolayer culture of a human melanoma), and the other indicated cell lines.

P-388 cells were seeded into 16 mm wells at $1\times10^4$ cells per well in 1 ml aliquots of MEM 5FCS containing the indicated concentration of drug. A separate set of cultures without drug were seeded as control of growth to ensure that cells remained in exponential phase of growth. All determinations were carried out duplicated. After three days of incubation at 37° in 10% CO2 atmosphere with 98% humidity, the wells were stained with 0.1% Crystal Violet. The IC50 was calculated by comparing the growth in wells with drug with the growth in control wells without the drug.

In Table 5 are presented the activity expressed as IC50 in mcg/ml

TABLE 5

| Compound | P-388 | P388MDR | MIEL8226 | A-549 | HT-29 | MEL-28 | CV1 |
| --- | --- | --- | --- | --- | --- | --- | --- |
| IB-96212 | 0.0001 | 0.001 | 0.005 | 1.00 | 1.00 | 1.00 | 0.0002 |
| IB-96212B | 0.001 | | | 1 | 1.2 | 1 | 0.001 |
| cis-platin | 2.5 | 2.5 | | 2.5 | 5 | 2.5 | |
| adriamicin | 0.02 | 1 | | 0.002 | 0.05 | 0.02 | |
| taxol | 0.2 | >2 | | 0.002 | 0.002 | 0.002 | |
| etopoxide | 0.1 | 10 | | 0.1 | 1 | 0.5 | |

The antimicrobial activity of compound IB-96212 was studied incubating the tested micro-organisms with IB-96212 in liquid Mueller-Hinton medium at 35° C. MIC was determined by the appearance of turbidity in the incubating medium after 24 hours of incubation with IB-96212. In Table 6 are shown these results. IB-96212 shows bactericidal activity against Gram-positive bacteria

TABLE 6

| Micro-organism | MIC($\mu$g/ml) |
| --- | --- |
| Escherichia coli | >100 |
| Klebsiella pneumoniae | >100 |
| Pseudomonas aeruginosa | >100 |
| Staphylococcus aureus | 100 |
| Bacillus subtilis | 100 |
| Micrococcus luteus | 0.4 |

REFERENCES

The following references have been cited herein, and they are hereby incorporated herein by reference:

(1) American Type Culture Catalog 17th edition 1989. Rockville, Md. U.S.A.

(2) Bergeron, et al. Biochem. Biophys. Res. Comm., 121:848, 1984

(3) Guerrant G. O., and C. W. Moss, Anal. Chem. 56:633, 1984

(4) Lechevalier M. P., et al. J. Bacteriol. 105:313, 1971

(5) Luedernann G. M. Personal Communication (6) Schroeder, et al., J. Med. Chem., 24:1078, 1981

(7) Shirling B. E., and D. Goblieb. Int. J. Syst. Bacteriol. 16:313, 1966

(8) Van der Auwera et al. J. Microbiol. Methods 4:265, 1986

(9) Waksman, S. A. The Actinomycetcs vol. II: 331, 1961

The present invention has been described in detail, including the preferred embodiments thereof. However, it will be appreciated that those skilled in the art, upon consideration of the present disclosure may make modifications and/or improvements.

What is claimed is:

1. A compound of the formula:

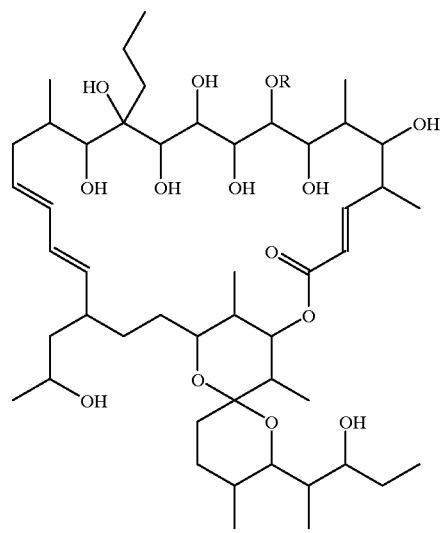

wherein R is hydrogen or a substituent group selected from the group consisting of a mono-, di- or tri-saccharide, C1–6 alky, C2–C7 acyl, cyclo-(C4–C8)-alkyl, phenyl, naphthyl, benzyl and a 4 to 8 membered heterocyclic group having 1 to 4 heteroatoms.

2. A compound of claim 1, being the compound referred to herein as IB-96212, having the structure:

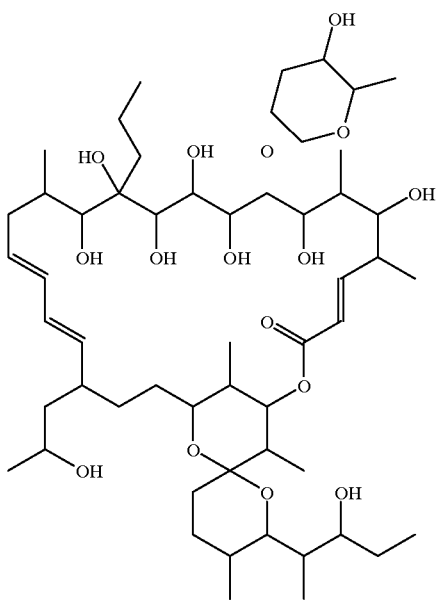

or the compound referred to herein as IB-96212B, having the structure:

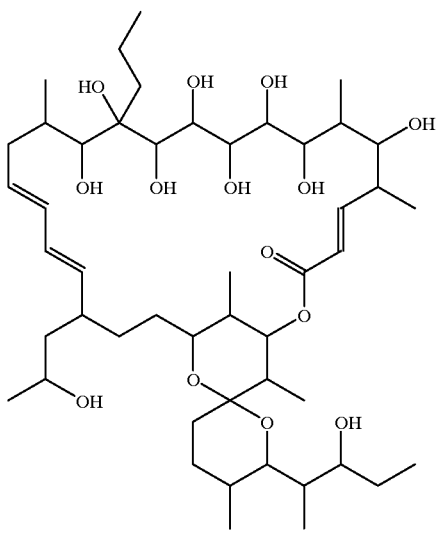

3. The compound referred to herein as IB-96212, said compound exhibiting spectral characteristics in which:
   FIG. 1 is a HPLC chromatogram of purified IB-96212;
   FIG. 2 is an ultraviolet spectrum (UV) of purified IB-96212;
   FIG. 3 is an infrared (IR) spectrum of purified IB-96212;
   FIG. 4 is a proton NMR ($^1$H) spectrum of purified IB-96212;
   FIG. 5 is a carbon-13 NMR ($^{13}$C) spectrum of purified B-96212; and
   FIG. 6 is a mass spectrum of purified IB-96212.

4. A process for producing the compound IB-96212, which comprises the step of:
   cultivating a strain of a microorganism capable of producing the compound IB-96212 in an aqueous nutrient medium under controlled conditions,
   wherein the microorganism comprises the culture strain of Micromonospora sp. ES25-008, and
   wherein the cultivation is conducted for sufficient time to form an isolatable quantity of the compound IB-96212.

5. The process of claim 4, which further comprises isolating and purifying the compound IB-96212 from the culture broth.

6. The process of claim 4 or 5, wherein the IB-96212 producing microorganism is cultivated under controlled submerged aerobic conditions with assimilable carbon, nitrogen and salt sources.

7. A process for producing the compound IB-96212B which comprises hydrolysis of the compound IB-96212.

8. A process for producing a compound according to claim 1 in which R is not hydrogen, which comprises the step of reacting the compound of claim 1 in which R is hydrogen, with a derivatizing agent to yield a compound in which R is a substituent group selected from the group consisting of a mono-, di- or tri-saccharide, C1–6 alkyl, C2–C7 acyl, cyclo-(C4–C8)-alkyl, phenyl, naphthyl, benzyl and a 4 to 8 membered heterocyclic group having 1 to 4 heteroatoms.

9. A method of treating mammalian tumors in patients in need of such treatment comprising administering an effective anti-tumor amount of a compound of claim 1 to said patient.

10. An antibacterial pharmaceutical composition comprising a compound according to claim 1 and a pharmaceutically acceptable carrier, diluent or excipient.

11. An antitumor pharmaceutical composition comprising the compound IB-96212 or IB-96212B in an amount effective against one or more mammalian tumors and a pharmaceutically acceptable carrier, diluent or excipient.

12. The biologically pure strain Micromonospora sp. ES25-008, available under the accession number CECT-3333.

13. A method of treating gram positive bacterial infections in patients in need of such treatment comprising administering an effective antibacterial amount of a compound of claim 1 to said patient.

* * * * *

UNITED STATES PATENT AND TRADEMARK OFFICE
CERTIFICATE OF CORRECTION

PATENT NO.    : 6,395,711 B1
DATED         : May 28, 2002
INVENTOR(S)   : Rosa Isabel Fernandez-Chimeno et al.

Figure 10:
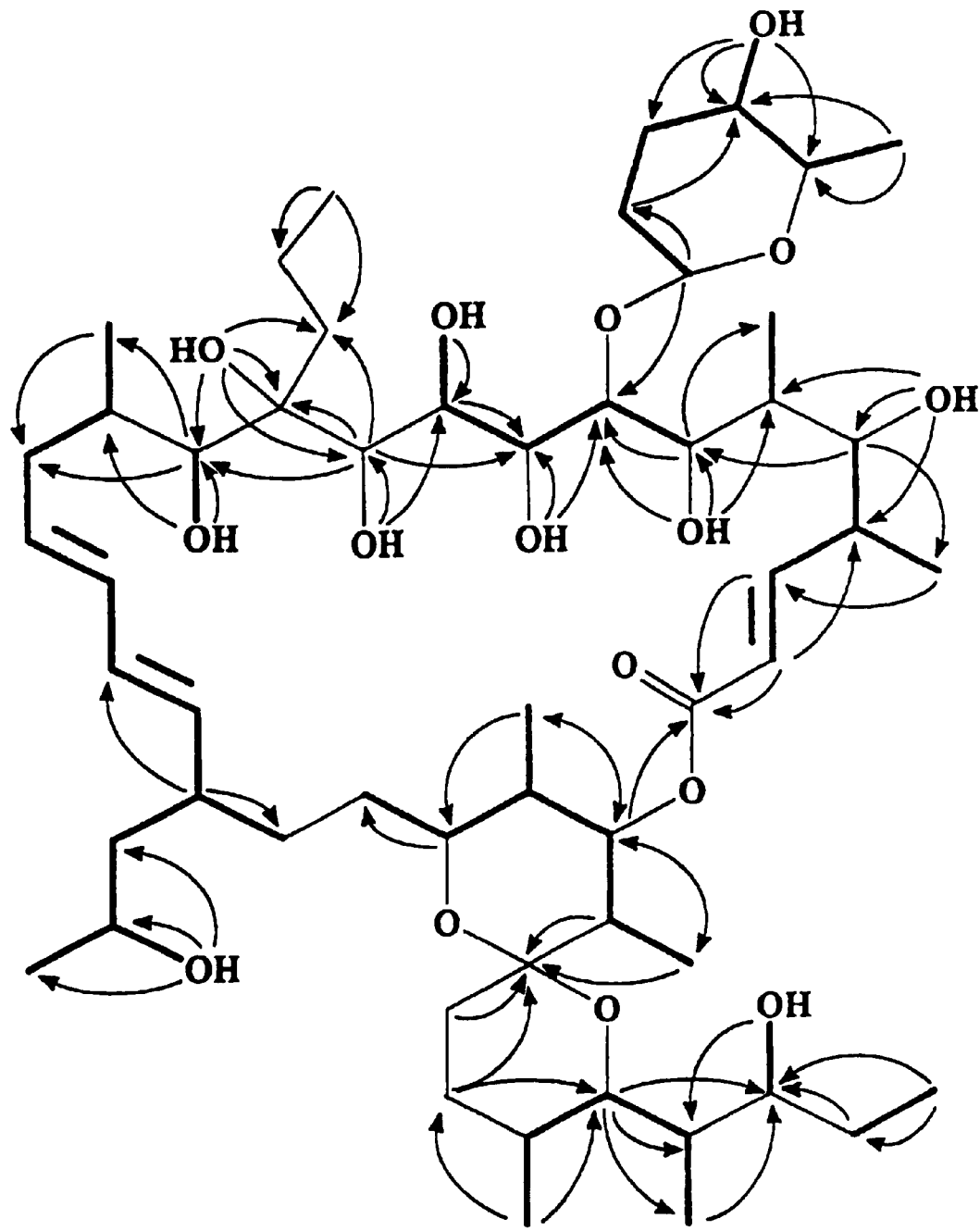
FIG. 10 shows the NMR correlations of IB-96212B.
Figure 11A:
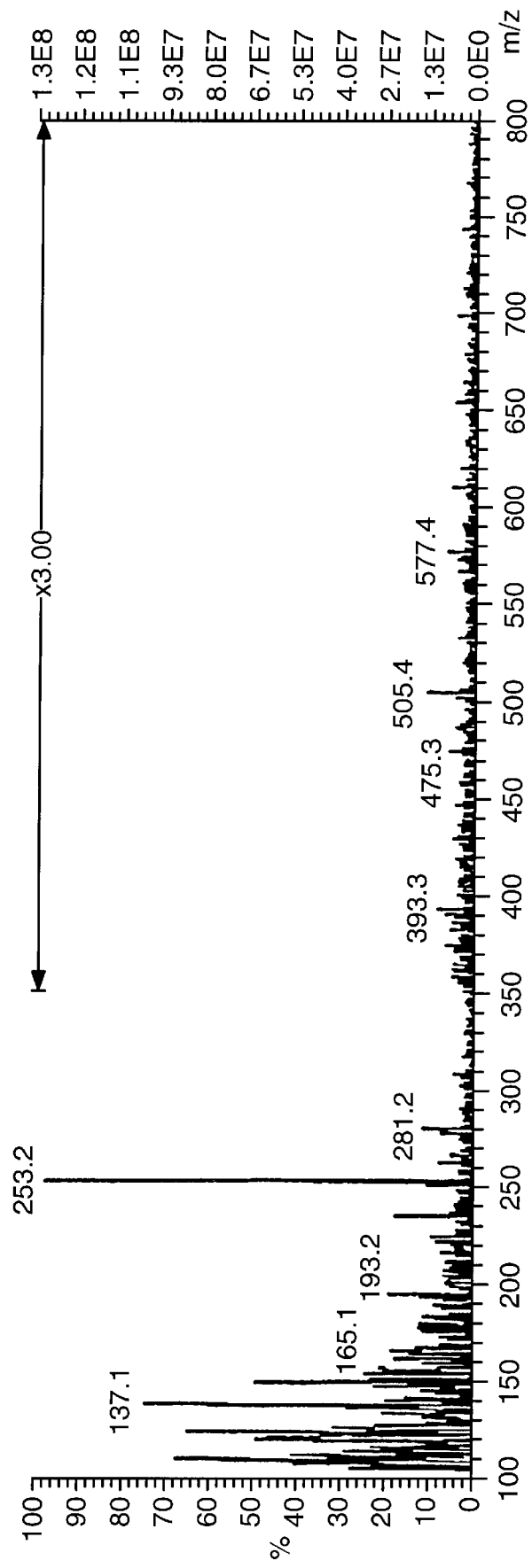
FIG. 11 is a mass spectrum of IB96212B.
Figure 11B:
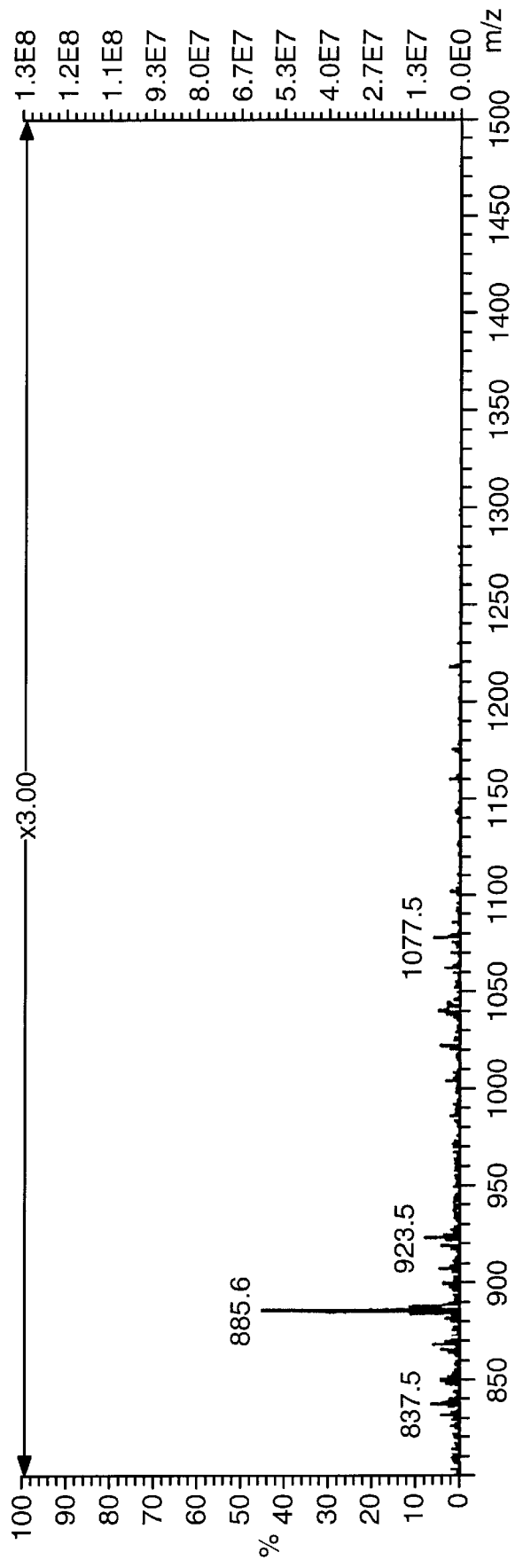
Figure 13:
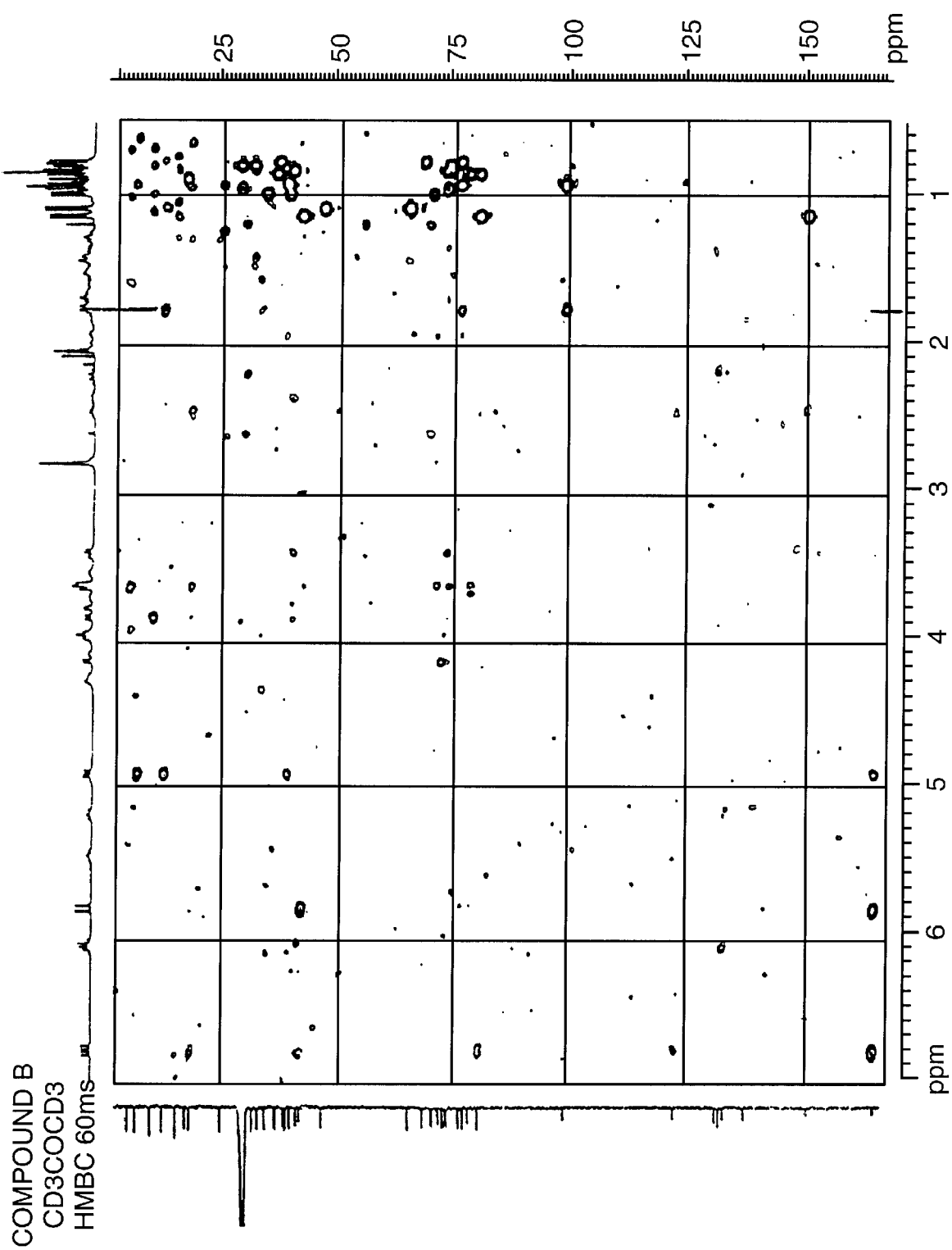
FIG. 13 is an HMBC 110 ms NMR spectrum of IB96212B taken in acetone-$d_6$.
Figure 14:
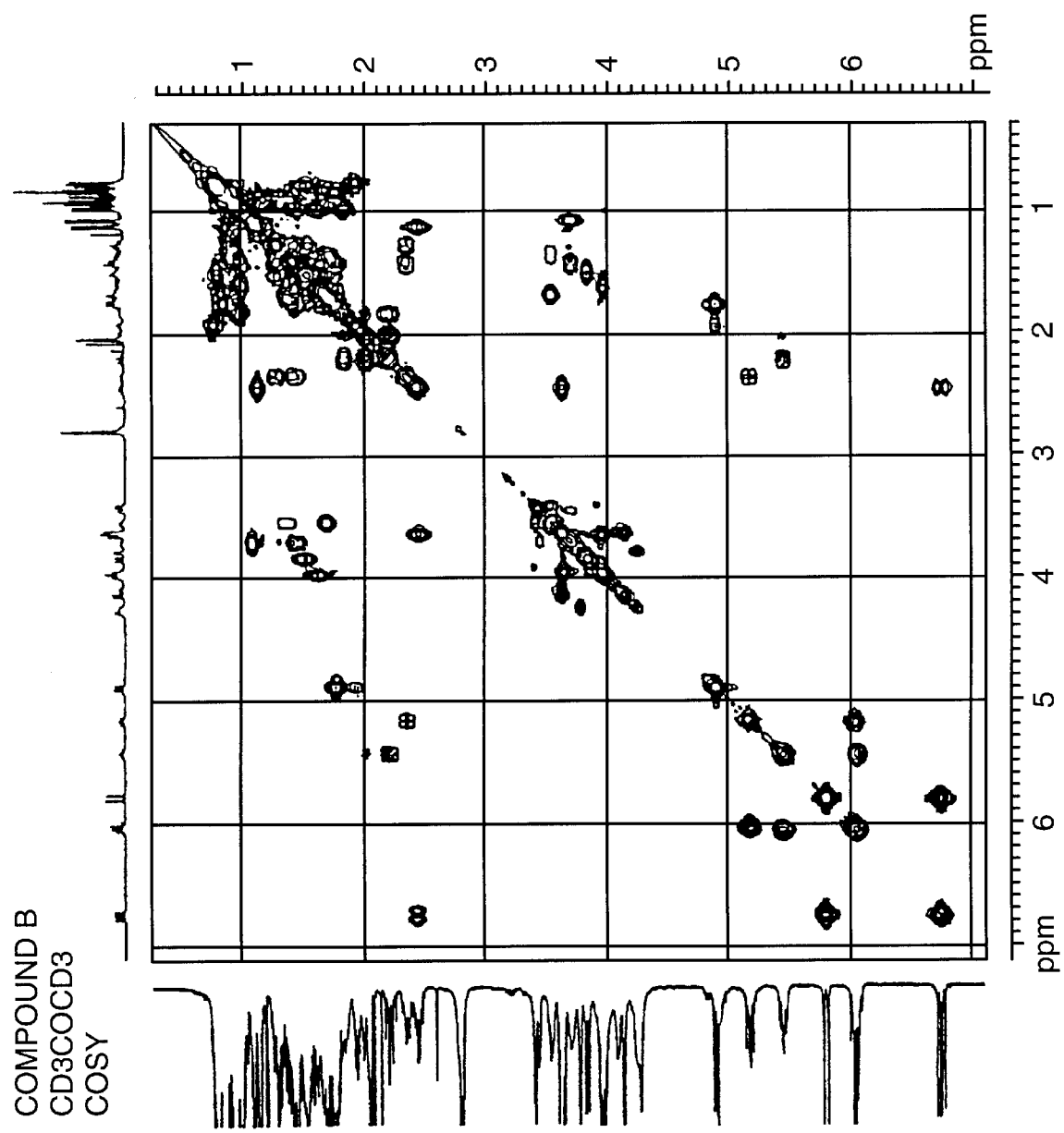
FIG. 14 is a COSY NMR spectrum of IB-96212B taken in acetone-$d_6$.
Figure 15:
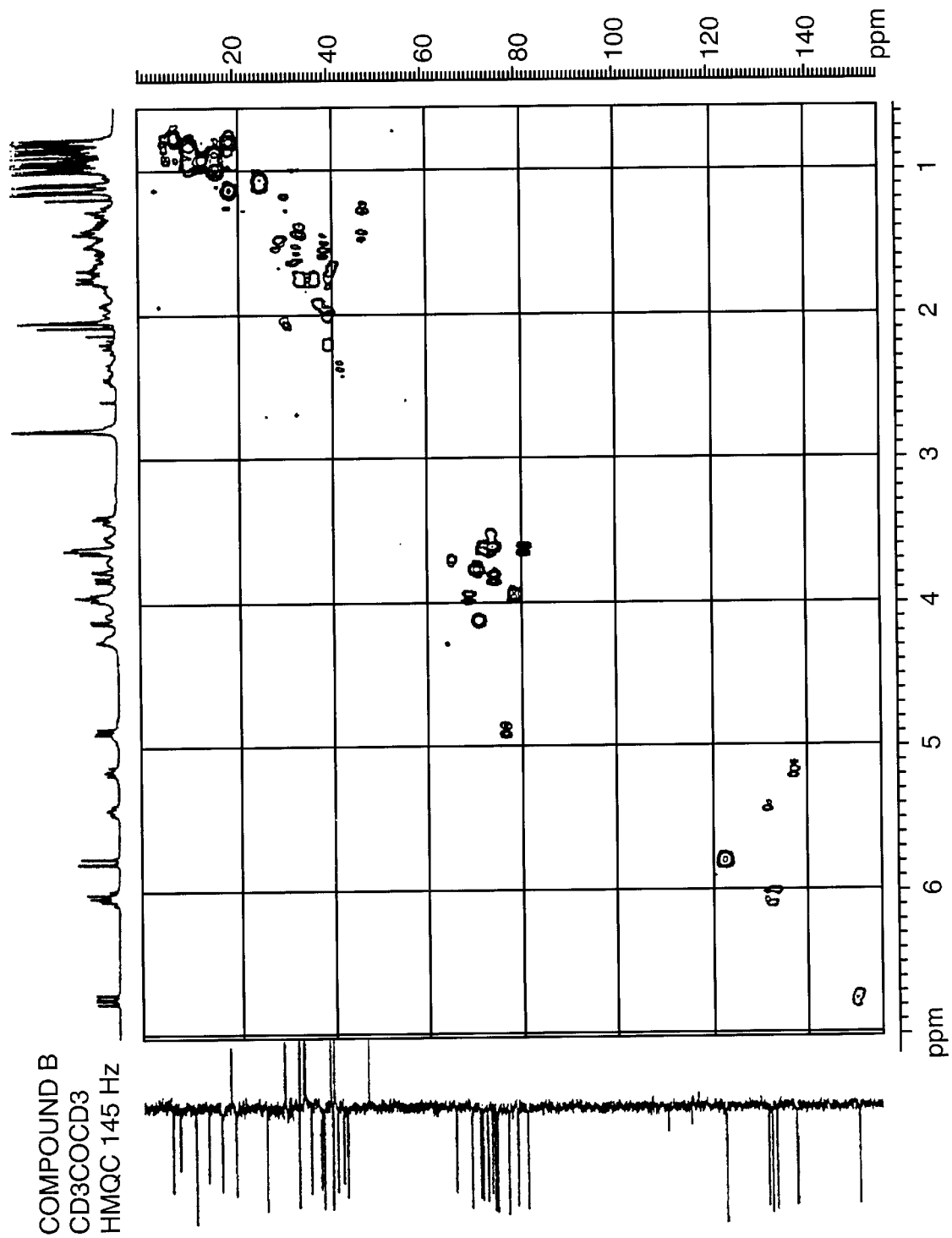
FIG. 15 is an HMQC 145 Hz NMR spectrum of IB-96212B taken in acetone-$d_6$.

It is certified that error appears in the above-identified patent and that said Letters Patent is hereby corrected as shown below:

<u>Title page,</u>
Item [57], ABSTRACT, please replace the formula (I), with the following corrected formula (I) which is shown in original Figure 10,

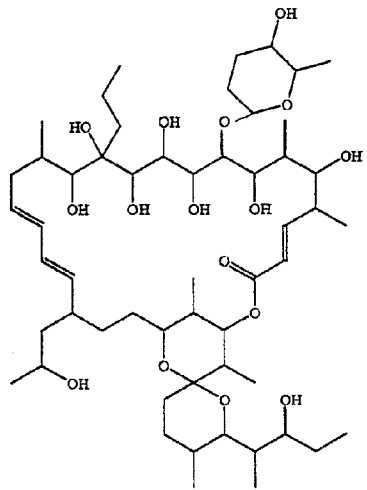

<u>Column 1</u>
Lines 40-60, please replace the formula (I), with the following corrected formula (I) which is shown in original Figure 10,

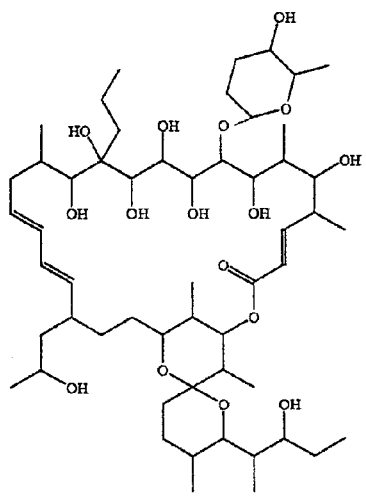

UNITED STATES PATENT AND TRADEMARK OFFICE
CERTIFICATE OF CORRECTION

PATENT NO.    : 6,395,711 B1
DATED         : May 28, 2002
INVENTOR(S)   : Rosa Isabel Fernandez-Chimeno et al.

It is certified that error appears in the above-identified patent and that said Letters Patent is hereby corrected as shown below:

Column 15,
Lines 8-33, please replace the formula (I), with the following corrected formula (I) which is shown in original Figure 10,

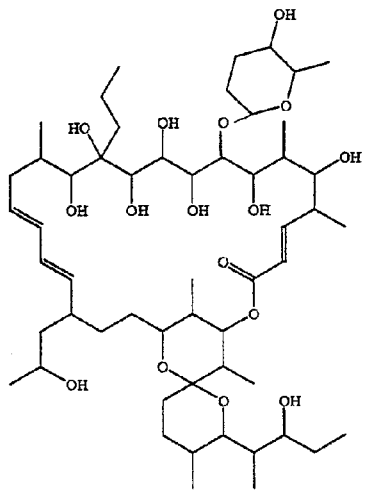

Signed and Sealed this

Twenty-second Day of October, 2002

Attest:

JAMES E. ROGAN
Attesting Officer    Director of the United States Patent and Trademark Office